US011521373B1

(12) United States Patent
Akbas et al.

(10) Patent No.: US 11,521,373 B1
(45) Date of Patent: Dec. 6, 2022

(54) SYSTEM FOR ESTIMATING A THREE DIMENSIONAL POSE OF ONE OR MORE PERSONS IN A SCENE

(71) Applicant: Bertec Corporation, Columbus, OH (US)

(72) Inventors: Emre Akbas, Ankara (TR); Batuhan Karagoz, Ankara (TR); Necip Berme, Worthington, OH (US); Mohan Chandra Baro, Columbus, OH (US)

(73) Assignee: Bertec Corporation, Columbus, OH (US)

( * ) Notice: Subject to any disclaimer, the term of this patent is extended or adjusted under 35 U.S.C. 154(b) by 0 days.

(21) Appl. No.: 17/827,975

(22) Filed: May 30, 2022

Related U.S. Application Data

(63) Continuation-in-part of application No. 17/533,096, filed on Nov. 22, 2021, now Pat. No. 11,348,279, (Continued)

(51) Int. Cl.
*G06K 9/00* (2022.01)
*G06V 10/82* (2022.01)
(Continued)

(52) U.S. Cl.
CPC ............... *G06V 10/82* (2022.01); *G06T 7/73* (2017.01); *G06V 10/76* (2022.01); *G06V 40/10* (2022.01);
(Continued)

(58) Field of Classification Search
CPC ........ G06V 10/82; G06V 10/76; G06V 40/10; G06V 2201/07; G06T 7/73;
(Continued)

(56) References Cited

U.S. PATENT DOCUMENTS

| 6,038,488 A | 3/2000 | Barnes et al. |
| 6,113,237 A | 9/2000 | Ober et al. |

(Continued)

OTHER PUBLICATIONS

Pavlakos, Georgios, Xiaowei Zhou, and Kostas Daniilidis. "Ordinal depth supervision for 3d human pose estimation." Proceedings of the IEEE Conference on Computer Vision and Pattern Recognition. (Year: 2018).*

(Continued)

*Primary Examiner* — Andrew M Moyer
(74) *Attorney, Agent, or Firm* — The Law Office of Patrick F. O'Reilly III, LLC

(57) ABSTRACT

A system for estimating a three dimensional pose of one or more persons in a scene is disclosed herein. The system includes one or more cameras and a data processor configured to execute computer executable instructions. The computer executable instructions include: (i) receiving one or more images of the scene from the one or more cameras; (ii) extracting features from the one or more images of the scene for providing inputs to a first branch pose estimation neural network and second branch pose estimation neural network; (iii) generating a first training signal from the second branch pose estimation neural network using a three dimensional reconstruction module for input into the first branch pose estimation neural network; (iv) generating one or more volumetric heatmaps; and (v) applying a maximization function to the one or more volumetric heatmaps to obtain a 3D pose of one or more persons in the scene.

12 Claims, 19 Drawing Sheets

Related U.S. Application Data which is a continuation-in-part of application No. 17/107,845, filed on Nov. 30, 2020, now Pat. No. 11,182,924, which is a continuation-in-part of application No. 16/826,200, filed on Mar. 21, 2020, now Pat. No. 10,853,970.

(60) Provisional application No. 62/822,352, filed on Mar. 22, 2019.

(51) Int. Cl.
   *G06V 40/10*    (2022.01)
   *G06V 10/75*    (2022.01)
   *G06T 7/73*     (2017.01)

(52) U.S. Cl.
   CPC ............ *G06T 2207/20081* (2013.01); *G06T 2207/20084* (2013.01); *G06T 2207/30196* (2013.01); *G06V 2201/07* (2022.01)

(58) Field of Classification Search
   CPC . G06T 2207/20081; G06T 2207/20084; G06T 2207/30196
   See application file for complete search history.

(56) References Cited

U.S. PATENT DOCUMENTS

| | | | |
|---|---|---|---|
| 6,152,564 A | 11/2000 | Ober et al. | |
| 6,295,878 B1 | 10/2001 | Berme | |
| 6,354,155 B1 | 3/2002 | Berme | |
| 6,389,883 B1 | 5/2002 | Berme et al. | |
| 6,936,016 B2 | 8/2005 | Berme et al. | |
| 8,181,541 B2 | 5/2012 | Berme | |
| 8,315,822 B2 | 11/2012 | Berme et al. | |
| 8,315,823 B2 | 11/2012 | Berme et al. | |
| D689,388 S | 9/2013 | Berme | |
| D689,389 S | 9/2013 | Berme | |
| 8,543,540 B1 | 9/2013 | Wilson et al. | |
| 8,544,347 B1 | 10/2013 | Berme | |
| 8,643,669 B1 | 2/2014 | Wilson et al. | |
| 8,700,569 B1 | 4/2014 | Wilson et al. | |
| 8,704,855 B1 | 4/2014 | Berme et al. | |
| 8,764,532 B1 | 7/2014 | Berme | |
| 8,847,989 B1 | 9/2014 | Berme et al. | |
| D715,669 S | 10/2014 | Berme | |
| 8,902,249 B1 | 12/2014 | Wilson et al. | |
| 8,915,149 B1 | 12/2014 | Berme | |
| 9,032,817 B2 | 5/2015 | Berme et al. | |
| 9,043,278 B1 | 5/2015 | Wilson et al. | |
| 9,066,667 B1 | 6/2015 | Berme et al. | |
| 9,081,436 B1 | 7/2015 | Berme et al. | |
| 9,168,420 B1 | 10/2015 | Berme et al. | |
| 9,173,596 B1 | 11/2015 | Berme et al. | |
| 9,200,897 B1 | 12/2015 | Wilson et al. | |
| 9,277,857 B1 | 3/2016 | Berme et al. | |
| D755,067 S | 5/2016 | Berme et al. | |
| 9,404,823 B1 | 8/2016 | Berme et al. | |
| 9,414,784 B1 | 8/2016 | Berme et al. | |
| 9,468,370 B1 | 10/2016 | Shearer | |
| 9,517,008 B1 | 12/2016 | Berme et al. | |
| 9,526,443 B1 | 12/2016 | Berme et al. | |
| 9,526,451 B1 | 12/2016 | Berme | |
| 9,558,399 B1 | 1/2017 | Jeka et al. | |
| 9,568,382 B1 | 2/2017 | Berme et al. | |
| 9,622,686 B1 | 4/2017 | Berme et al. | |
| 9,763,604 B1 | 9/2017 | Berme et al. | |
| 9,770,203 B1 | 9/2017 | Berme et al. | |
| 9,778,119 B2 | 10/2017 | Berme et al. | |
| 9,814,430 B1 | 11/2017 | Berme et al. | |
| 9,829,311 B1 | 11/2017 | Wilson et al. | |
| 9,854,997 B1 | 1/2018 | Berme et al. | |
| 9,916,011 B1 | 3/2018 | Berme et al. | |
| 9,927,312 B1 | 3/2018 | Berme et al. | |
| 10,010,248 B1 | 7/2018 | Shearer | |
| 10,010,286 B1 | 7/2018 | Berme et al. | |
| 10,085,676 B1 | 10/2018 | Berme et al. | |
| 10,117,602 B1 | 11/2018 | Berme et al. | |
| 10,126,186 B2 | 11/2018 | Berme et al. | |
| 10,216,262 B1 | 2/2019 | Berme et al. | |
| 10,231,662 B1 | 3/2019 | Berme et al. | |
| 10,264,964 B1 | 4/2019 | Berme et al. | |
| 10,331,324 B1 | 6/2019 | Wilson et al. | |
| 10,342,473 B1 | 7/2019 | Berme et al. | |
| 10,390,736 B1 | 8/2019 | Berme et al. | |
| 10,413,230 B1 | 9/2019 | Berme et al. | |
| 10,463,250 B1 | 11/2019 | Berme et al. | |
| 10,527,508 B2 | 1/2020 | Berme et al. | |
| 10,555,688 B1 | 2/2020 | Berme et al. | |
| 10,646,153 B1 | 5/2020 | Berme et al. | |
| 10,722,114 B1 | 7/2020 | Berme et al. | |
| 10,736,545 B1 | 8/2020 | Berme et al. | |
| 10,765,936 B2 | 9/2020 | Berme et al. | |
| 10,803,616 B1* | 10/2020 | Twigg | G06F 3/016 |
| 10,803,990 B1 | 10/2020 | Wilson et al. | |
| 10,853,970 B1 | 12/2020 | Akbas et al. | |
| 10,856,796 B1 | 12/2020 | Berme et al. | |
| 10,860,843 B1 | 12/2020 | Berme et al. | |
| 10,945,599 B1 | 3/2021 | Berme et al. | |
| 10,966,606 B1 | 4/2021 | Berme | |
| 11,033,453 B1 | 6/2021 | Berme et al. | |
| 11,052,288 B1 | 7/2021 | Berme et al. | |
| 11,054,325 B2 | 7/2021 | Berme et al. | |
| 11,074,711 B1 | 7/2021 | Akbas et al. | |
| 11,097,154 B1 | 8/2021 | Berme et al. | |
| 11,158,422 B1 | 10/2021 | Wilson et al. | |
| 11,182,924 B1 | 11/2021 | Akbas et al. | |
| 11,262,231 B1 | 3/2022 | Berme et al. | |
| 11,262,258 B2 | 3/2022 | Berme et al. | |
| 11,301,045 B1 | 4/2022 | Berme et al. | |
| 11,311,209 B1 | 4/2022 | Berme et al. | |
| 11,321,868 B1 | 5/2022 | Akbas et al. | |
| 11,337,606 B1 | 5/2022 | Berme et al. | |
| 11,348,279 B1 | 5/2022 | Akbas et al. | |
| 2003/0216656 A1 | 11/2003 | Berme et al. | |
| 2008/0228110 A1 | 9/2008 | Berme | |
| 2011/0277562 A1 | 11/2011 | Berme | |
| 2012/0266648 A1 | 10/2012 | Berme et al. | |
| 2012/0271565 A1 | 10/2012 | Berme et al. | |
| 2013/0230211 A1 | 9/2013 | Tanabiki et al. | |
| 2015/0096387 A1 | 4/2015 | Berme et al. | |
| 2015/0143627 A1 | 5/2015 | McBride | |
| 2016/0106360 A1 | 4/2016 | Choi et al. | |
| 2016/0245711 A1 | 8/2016 | Berme et al. | |
| 2016/0334288 A1 | 11/2016 | Berme et al. | |
| 2018/0021629 A1 | 1/2018 | DeLuca et al. | |
| 2018/0024015 A1 | 1/2018 | Berme et al. | |
| 2019/0078951 A1 | 3/2019 | Berme et al. | |
| 2019/0099134 A1 | 4/2019 | Bennett et al. | |
| 2020/0139229 A1 | 5/2020 | Berme et al. | |
| 2020/0160535 A1 | 5/2020 | Akbarian et al. | |
| 2020/0408625 A1 | 12/2020 | Berme et al. | |
| 2021/0333163 A1 | 10/2021 | Berme et al. | |
| 2022/0178775 A1 | 6/2022 | Berme et al. | |

OTHER PUBLICATIONS

Nibali, A., He, Z., Morgan, S., & Prendergast, L. (Jan. 2019). 3d human pose estimation with 2d marginal heatmaps. In 2019 IEEE Winter Conference on Applications of Computer Vision (WACV) (pp. 1477-1485). IEEE (Year: 2019).*

S. Amin, M. Andriluka, M. Rohrbach, and B. Schiele. Multiview pictorial structures for 3d human pose estimation. In British Machine Vision Conference. (Jan. 2013) pp. 1-12.

M. Andriluka, L. Pishchulin, P. Gehler, and B. Schiele. 2D human pose estimation: New benchmark and state of the art analysis. In IEEE Conference on Computer Vision and Pattern Recognition. (Jun. 2014) pp. 1-8.

V. Belagiannis, S. Amin, M. Andriluka, B. Schiele, N. Navab, and S. Ilic. 3D pictorial structures for multiple human pose estimation. In IEEE Conference on Computer Vision and Pattern Recognition. (Jun. 2014) pp. 1-8.

(56) References Cited

OTHER PUBLICATIONS

V. Belagiannis, S. Amin, M. Andriluka, B. Schiele, N. Navab, and S. Ilic. 3D pictorial structures revisited: Multiple human pose estimation. IEEE Transaction on Pattern Analysis and Machine Intelligence. (Oct. 2016) pp. 1-14.
M. Bergtholdt, J. Kappes, S. Schmidt, and C. Schnorr. A study of parts-based object class detection using complete graphs. In International Journal of Computer Vision. (Mar. 2010) pp. 1-25.
M. Burenius, J. Sullivan, and S. Carlsson. 3D pictorial structures for multiple view articulated pose estimation. In IEEE Conference on Computer Vision and Pattern Recognition. (Jun. 2013) pp. 3618-3625.
Z. Cao, T. Simon, S.-E. Wei, and Y. Sheikh. Realtime multiperson 2d pose estimation using part affinity fields. In IEEE Conference on Computer Vision and Pattern Recognition. (Nov. 2016) pp. 7291-7299.
C.-H. Chen and D. Ramanan. 3D human pose estimation = 2D pose estimation + matching. In IEEE Conference on Computer Vision and Pattern Recognition. (Jul. 2017) pp. 7035-7043.
D. Drover, R. MV, C.-H. Chen, A. Agrawal, A. Tyagi, and C. P. Huynh. Can 3d pose be learned from 2d projections alone? European Conference on Computer Vision Workshops (Aug. 2018) pp. 1-17.
A. Elhayek, E. de Aguiar, A. Jain, J. Thompson, L. Pishchulin, M. Andriluka, C. Bregler, B. Schiele, and C. Theobalt. MARCOnl—ConvNet-based MARker-less motion capture in outdoor and indoor scenes. IEEE Transaction on Pattern Analysis and Machine Intelligence. (Mar. 2017) pp. 501-514.
A. Elhayek, E. de Aguiar, A. Jain, J. Tompson, L. Pishchulin, M. Andriluka, C. Bregler, B. Schiele, and C. Theobalt. Efficient ConvNet-based marker-less motion capture in general scenes with a low number of cameras. In IEEE Conference on Computer Vision and Pattern Recognition. (Jun. 2015) pp. 3810-3818.
H.-S. Fang, Y. Xu, W. Wang, X. Liu, and S.-C. Zhu. Learning pose grammar to encode human body configuration for 3D pose estimation. In Association for the Advancement of Artificial Intelligence. (Jan. 2018) pp. 1-8.
R. I. Hartley and P. Sturm. Triangulation. Computer Vision and Image Understanding. (Nov. 1997) pp. 146-157.
K. He, X. Zhang, S. Ren, and J. Sun. Deep residual learning for image recognition. In IEEE Conference on Computer Vision and Pattern Recognition. (Jun. 2016) pp. 770-778.
S. Ioffe and C. Szegedy. Batch normalization: Accelerating deep network training by reducing internal covariate shift. In Journal of Machine Learning Research. (Mar. 2015) pp. 1-11.
C. Ionescu, D. Papava, V. Olaru, and C. Sminchisescu. Human3.6m: Large scale datasets and predictive methods for 3D human sensing in natural environments. In IEEE Transaction on Pattern Analysis and Machine Intelligence. (Dec. 2013) pp. 1-15.
D. P. Kingma and J. Ba. Adam: A method for stochastic optimization. In International Conference on Learning Representations. (Dec. 2014) pp. 1-15.
M. Kocabas, S. Karagoz, and E. Akbas. Multiposenet: Fast multiperson pose estimation using pose residual network. In European Conference on Computer Vision. (Jul. 2018) pp. 1-17.
S. Li and A. B. Chan. 3D human pose estimation from monocular images with deep convolutional neural network. In Asian Conference on Computer Vision (Nov. 2014) pp. 1-16.
T.-Y. Lin, M. Maire, S. Belongie, J. Hays, P. Perona, D. Ramanan, P. Dollar, and C. L. Zitnick. Microsoft COCO: Common objects in context. In European Conference on Computer Vision. (May 2014) pp. 1-15.
A. L. Maas, A. Y. Hannun, and A. Y. Ng. Rectifier nonlinearities improve neural network acoustic models. In International Conference on Machine Learning (Jun. 2013) pp. 1-6.
J. Martinez, R. Hossain, J. Romero, and J. J. Little. A simple yet effective baseline for 3D human pose estimation. In International Conference on Computer Vision. (Aug. 2017) pp. 1-10.
D. Mehta, H. Rhodin, D. Casas, P. Fua, O. Sotnychenko, W. Xu, and C. Theobalt. Monocular 3D human pose estimation in the wild using improved CNN supervision. In International Conference on 3DVision. (Oct. 2017) pp. 1-16.
F. Moreno-Noguer. 3D human pose estimation from a single image via distance matrix regression. In IEEE Conference on Computer Vision and Pattern Recognition. (Nov. 2016) pp. 1-10.
A. Newell, K. Yang, and J. Deng. Stacked hourglass networks for human pose estimation. In European Conference an Computer Vision. (Jul. 2016) pp. 1-17.
D. Nister. An efficient solution to the five-point relative pose problem. IEEE Transaction on Pattern Analysis and Machine Intelligence. (Jun. 2004) pp. 1-8.
A. Paszke, S. Gross, S. Chintala, G. Chanan, E. Yang, Z. De-Vito, Z. Lin, A. Desmaison, L. Antiga, and A. Lerer. Automatic differentiation in pytorch. In International Conference on Learning Representations. (Oct. 2017) pp. 1-4.
G. Pavlakos, X. Zhou, and K. Daniilidis. Ordinal depth supervision for 3D human pose estimation. In IEEE Conference on Computer Vision and Pattern Recognition. (Jun. 2018) pp. 7307-7316.
G. Pavlakos, X. Zhou, K. G. Derpanis, and K. Daniilidis. Coarse-to-fine volumetric prediction for single-image 3D human pose. In IEEE Conference on Computer Vision and Pattern Recognition. (Jul. 2017) pp. 1-10.
G. Pavlakos, X. Zhou, K. G. Derpanis, and K. Daniilidis. Harvesting multiple views for marker-less 3d human pose annotations. In IEEE Conference on Computer Vision and Pattern Recognition. (Jul. 2017) pp. 6988-6997.
H. Rhodin, J. Sporri, I. Katircioglu, V. Constantin, F. Meyer, E. Muller, M. Salzmann, and P. Fua. Learning monocular 3d human pose estimation from multi-view images. In IEEE Conference on Computer Vision and Pattern Recognition. (Mar. 2018) pp. 1-10.
G. Rogez, P. Weinzaepfel, and C. Schmid. Lcr-net: Localization-classification-regression for human pose. In IEEE Conference on Computer Vision and Pattern Recognition. (Jul. 2017) pp. 3433 3441.
M. Sanzari, V. Ntouskos, and F. Pirri. Bayesian image based 3d pose estimation. In European Conference on Computer Vision. (Oct. 2016), one page.
I. Sarandi, T. Linder, K. O. Arras, and B. Leibe. How robust is 3d human pose estimation to occlusion? In IROS Workshop—Robotic Co-workers 4.0. (Aug. 2018) pp. 1-5.
X. Sun, J. Shang, S. Liang, and Y. Wei. Compositional human pose regression. In International Conference on Computer Vision. (Aug. 2017) pp. 1-11.
X. Sun, B. Xiao, F. Wei, S. Liang, and Y. Wei. Integral human pose regression. In European Conference on Computer Vision. (Sep. 2018) pp. 1-17.
S. Suwajanakorn, N. Snavely, J. Tompson, and M. Norouzi. Discovery of latent 3d keypoints via end-to-end geometric reasoning. In Advances in Neural Information Processing. (Nov. 2018) pp. 1-14.
T. Kulkarni, W. Whitney, P. Kohli, and J. Tenenbaum. Deep convolutional inverse graphics network. In Advances in Neural Information Processing. (Jun. 2015) pp. 1-10.
B. Tekin, I. Katircioglu, M. Salzmann, V. Lepetit, and P. Fua. Structured prediction of 3D human pose with deep neural networks. In British Machine Vision Conference (May 2016) pp. 1-11.
B. Tekin, P. Marquez-Neila, M. Salzmann, and P. Fua. Learning to fuse 2D and 3D image cues for monocular body pose estimation. In International Conference on Computer Vision. (Apr. 2017) pp. 1-13.
D. Tome, C. Russell, and L. Agapito. Lifting from the deep: Convolutional 3D pose estimation from a single image. In IEEE Conference on Computer Vision and Pattern Recognition. (Jul. 2017) pp. 2500-2509.
H.-Y. F. Tung, A. W. Harley, W. Seto, and K. Fragkiadaki. Adversarial inverse graphics networks: Learning 2d-to-3d lifting and image-to-image translation from unpaired supervision. In International Conference on Computer Vision. (Sep. 2017) pp. 1-14.
L. van der Maaten and G. Hinton. Visualizing data using t-sne. In Journal of Machine Learning Research. (Nov. 2008) pp. 2579-2605.

(56) References Cited

OTHER PUBLICATIONS

S.-E. Wei, V. Ramakrishna, T. Kanade, and Y. Sheikh. Convolutional pose machines. In IEEE Conference on Computer Vision and Pattern Recognition. (Apr. 2016) pp. 1-9.
J. Wu, T. Xue, J. J. Lim, Y. Tian, J. B. Tenenbaum, A. Torralba, and W. T. Freeman. Single image 3d interpreter network. In European Conference on Computer Vision (ECCV). (Apr. 2016) pp. 1-17.
B. Xiaohan Nie, P. Wei, and S.-C. Zhu. Monocular 3d human pose estimation by predicting depth on joints. In International Conference on Computer Vision. (Oct. 2017) pp. 3467-3475.
X. Zhou, M. Zhu, K. Derpanis, and K. Daniilidis. Sparseness meets deepness: 3D human pose estimation from monocular video. In IEEE Conference on Computer Vision and Pattern Recognition. (Apr. 2016) pp. 1-10.
Pavlakos, Georgios, Xiaowei Zhou, and Kostas Daniilidis. "Ordinal depth supervision for 3d human pose estimation." Proceedings of the IEEE Conference on Computer Vision and Pattern Recognition 2018. (Year: 2018).
First office action on the merits (Non-Final Rejection) in U.S. Appl. No. 16/826,200, dated Apr. 27, 2020.
Notice of Allowance in U.S. Appl. No. 16/826,200, dated Aug. 3, 2020.
First office action on the merits (Non-Final Rejection) in U.S. Appl. No. 17/107,845, dated Jan. 22, 2021.
Second office action on the merits (Final Rejection) in U.S. Appl. No. 17/107,845, dated Apr. 1, 2021.
Notice of Allowance in U.S. Appl. No. 17/107,845, dated Jul. 16, 2021.
Notice of Allowance in U.S. Appl. No. 17/533,096, dated Feb. 3, 2022.

\* cited by examiner

Table 1. Triangulation results on H36M. Effects of different 2D keypoint sources on triangulation performance. *GT 2D* denotes the usage of ground truth 2D labels. *H36M 2D* and *MPII 2D* shows the pose estimation models trained on those datasets.

| Methods | MPJPE | NMPJPE | PMPJPE | PSS@50 | PSS@100 |
|---|---|---|---|---|---|
| Pavlakos et al. [30] | 56.89 | - | - | - | - |
| GT 2D | 4.38 | 2.87 | 2.13 | 98.93 | 97.16 |
| GT 2D (w/o R) | n/a | 22.46 | 15.06 | 98.83 | 96.03 |
| H36M 2D | 28.37 | 26.28 | 25.19 | 95.08 | 94.2 |
| MPII 2D | 45.86 | 37.79 | 36.83 | 90.06 | 85.96 |

FIG. 8

Table 2. H36M results. Top: Comparison of results between our methods trained with different settings and the state-of-the-art fully supervised methods. (*FS*: fully supervised, *SS*: self supervised) Bottom: Effect of adding refinement unit (RU) over SS. (* uses the 2D keypoints from an MPII pre trained model as input, hence is comparable to our SS+RU model.)

Supervised training on all subjects of H36M

| Methods | MPJPE | NMPJPE | PMPJPE | PSS@50 | PSS@100 |
|---|---|---|---|---|---|
| Nie et al. [46] (ICCV'17) | 97.5 | - | 79.5 | - | - |
| Sanzari et al. [33] (ECCV'16) | 93.1 | - | - | - | - |
| Tome et al. [41] (CVPR'17) | 88.4 | - | - | 73.0 | 58.8 |
| Rogez et al. [32] (CVPR'17) | 87.7 | - | 71.6 | - | - |
| Pavlakos et al. [29] (CVPR'17) | 71.9 | - | - | 74.05 | 53.93 |
| Rhodin et al. [31] (CVPR'18) | 66.8 | 63.3 | 51.6 | - | - |
| Martinez et al. [22] (ICCV'17) | 62.9 | - | 47.7 | 78.12 | 73.26 |
| Pavlakos et al. [28] (CVPR'18) | 56.2 | - | - | 80.03 | 69.18 |
| Sun et al. [36] (ECCV'18) | 49.6 | - | 40.6 | - | - |
| Ours FS | 52.82 | 52.49 | 45.15 | 84.44 | 78.67 |
| Ours SS | 76.82 | 75.53 | 67.48 | 73.09 | 64.03 |
| Ours (w/o R) | n/a | 78.83 | 69.54 | 70.67 | 62.05 |

Integrating Refinement Unit with SS trained network on H36M

| Methods | MPJPE | NMPJPE | PMPJPE | PSS@50 | PSS@100 |
|---|---|---|---|---|---|
| Martinez et al. [22] (ICCV'2017)* | 67.5 | - | 52.5 | - | - |
| Ours SS + RU | 60.06 | 60.04 | 46.85 | 80.42 | 75.41 |

FIG. 9

Table 3. H36M weakly/self supervised results. Top: Methods that can be trained without 3D ground truth labels. (Tung et al. [42] uses unpaired 3D supervision which is easier to get. *3DInterp* denotes the results of [45] implemented by [42]. *2D GT* denotes training with triangulations obtained from ground truth 2D labels.) Middle: Methods requiring a small set of ground truth data. (S1 denotes using ground truth labels of H36M subject #1 during training.) Bottom: Comparison to Drover et al. [9] that evaluated using 14 joints (14j))

Training without ground truth data

| Methods | MPJPE | NMPJPE | PMPJPE | PSS@50 | PSS@100 |
|---|---|---|---|---|---|
| Pavlakos et al. [30] (CVPR'2017) | 118.41 | - | - | - | - |
| Tung et al.- 3DInterp [42] (ICCV'2017) | 98.4 | - | - | - | - |
| Tung et al. [42] (ICCV'2017) | 97.2 | - | - | - | - |
| Ours SS | 76.82 | 75.53 | 67.48 | 73.09 | 64.03 |
| Ours SS (w/o R) | n/a | 78.83 | 69.54 | 70.67 | 62.05 |
| Ours SS (2D GT) | 55.69 | 55.5 | 48.27 | 83.9 | 78.69 |

Training with only Subject 1 of H36M

| Methods | MPJPE | NMPJPE | PMPJPE | PSS@50 | PSS@100 |
|---|---|---|---|---|---|
| Rhodin et al. [31] S1 | n/a | 78.2 | 64.6 | - | - |
| Rhodin et al. [31] S1 (w/o R) | n/a | 80.1 | 65.1 | - | - |
| Ours S1 | 65.58 | 64.92 | 57.22 | 81.91 | 75.2 |
| Ours S1 (w/o R) | n/a | 66.98 | 60.16 | 77.65 | 72.4 |

Evaluation using 14 joints

| Methods | MPJPE | NMPJPE | PMPJPE | PSS@50 | PSS@100 |
|---|---|---|---|---|---|
| Drover et al. [9](14j) (ECCVW'2018) | - | - | 64.6 | - | - |
| Ours SS (14j) | 70.09 | 68.15 | 60.27 | n/a | n/a |

FIG. 10

Table 4. 3DHP results. Top: Fully supervised training results. Middle: Self supervised learning using only subject 1. Bottom: Self supervised training without any ground truth examples.

Supervised training

| Methods | MPJPE | NMPJPE | PCK | NPCK | PSS@50 | PSS@100 |
|---|---|---|---|---|---|---|
| Mehta et al. [23] | - | - | 72.5 | - | - | - |
| Rhodin et al. [31] FS | n/a | 101.5 | n/a | 78.8 | - | - |
| Ours FS | 108.99 | 106.38 | 77.5 | 78.1 | 87.15 | 82.21 |

Training with only Subject 1 of 3DHP

| Methods | MPJPE | NMPJPE | PCK | NPCK | PSS@50 | PSS@100 |
|---|---|---|---|---|---|---|
| Rhodin et al. [31] S1 | n/a | 119.8 | n/a | 73.1 | - | - |
| Rhodin et al. [31] S1 (w/o R) | n/a | 121.8 | n/a | 72.7 | - | - |
| Ours S1 | n/a | 115.37 | n/a | 74.4 | 75.64 | 73.15 |
| Ours S1 (w/o R) | n/a | 119.86 | n/a | 73.5 | 73.41 | 70.97 |

Training without ground truth data

| Methods | MPJPE | NMPJPE | PCK | NPCK | PSS@50 | PSS@100 |
|---|---|---|---|---|---|---|
| Ours SS | 126.79 | 125.65 | 64.7 | 71.9 | 70.94 | 67.58 |

FIG. 11

SYSTEM FOR ESTIMATING A THREE DIMENSIONAL POSE OF ONE OR MORE PERSONS IN A SCENE

CROSS-REFERENCE TO RELATED APPLICATIONS

This is a continuation-in-part of U.S. Nonprovisional patent application Ser. No. 17/533,096, entitled "System for Estimating a Three Dimensional Pose of One or More Persons in a Scene", filed on Nov. 22, 2021; which is a continuation-in-part of U.S. Nonprovisional patent application Ser. No. 17/107,845, entitled "System for Estimating a Three Dimensional Pose of One or More Persons in a Scene", filed on Nov. 30, 2020, now U.S. Pat. No. 11,182,924; which is a continuation-in-part of U.S. Nonprovisional patent application Ser. No. 16/826,200, entitled "System for Estimating a Three Dimensional Pose of One or More Persons in a Scene", filed on Mar. 21, 2020, now U.S. Pat. No. 10,853,970; which claims the benefit of U.S. Provisional Patent Application No. 62/822,352, entitled "System for Estimating a Three Dimensional Pose of One or More Persons in a Scene", filed on Mar. 22, 2019, the disclosure of each of which is hereby incorporated by reference as if set forth in their entireties herein.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to a pose estimation system. More particularly, the invention relates to a system for estimating three-dimensional (3D) poses of one or more persons in a scene.

2. Background

Human pose estimation in the wild is a challenging problem in computer vision. Although there are large-scale datasets (see refs. [2, 20]) for two-dimensional (2D) pose estimation, 3D datasets (see refs. [16, 23]) are either limited to laboratory settings or limited in size and diversity. Since collecting 3D human pose annotations in the wild is costly and 3D datasets are limited, researchers have resorted to weakly or self-supervised approaches with the goal of obtaining an accurate 3D pose estimator by using minimal amount of additional supervision on top of the existing 2D pose datasets. Various methods have been developed to this end. These methods, in addition to ground-truth 2D poses, require either additional supervision in various forms (such as unpaired 3D ground truth data (see ref. [42]), a small subset of labels (see ref. [31])) or (extrinsic) camera parameters in multiview settings (see ref. [30]). To the best of our knowledge, there is only one method (see ref. [9]) which can produce a 3D pose estimator by using only 2D ground-truth. In the present patent application, another such method is described.

Initially, in order to put the present invention into context, single-view (during both training and inference) and entirely multi-view methods will be briefly described. In many recent works, convolutional neural networks (CNN) are used to estimate the coordinates of the 3D joints directly from images (see refs. [23, 35, 39, 40, 41]). Li and Chan (see ref. [19]) were the first to show that deep neural networks can achieve a reasonable accuracy in 3D human pose estimation from a single image. They used two deep regression networks and body part detection. Tekin et al. (see ref. [39]) show that combining traditional CNNs for supervised learning with auto-encoders for structure learning can yield good results. Contrary to common regression practice, Pavlakos et al. (see ref. [29]) were the first to consider 3D human pose estimation as a 3D keypoint localization problem in a voxel space. Recently, "integral pose regression" proposed by Sun et al. (see ref. [36]) combined volumetric heat maps with a soft-argmax activation and obtained state-of-the-art results.

Additionally, there are two-stage approaches which decompose the 3D pose inference task into two independent stages: estimating 2D poses, and lifting them into 3D space (see refs. [8], [12], [18], [22], [23], [24], [41], [47]). Most recent methods in this category use state-of-the-art 2D pose estimators (see refs. [7], [18], [25], [44]) to obtain joint locations in the image plane. Martinez et al. (see ref. [22]) use a simple deep neural network that can estimate 3D pose given the estimated 2D pose computed by a state-of-the-art 2D pose estimator. Pavlakos (see ref. [28]) proposed the idea of using ordinal depth relations among joints to bypass the need for full 3D supervision.

Methods in the aforedescribed single-view category require either full 3D supervision or extra supervision (e.g., ordinal depth) in addition to full 3D supervision. Output data from a motion capture system or inertial measurement units are typically used for full 3D supervision.

Methods in the multi-view category require multi-view input both during inference and training. Early work (see refs. [1], [3], [4], [5], [6]) used 2D pose estimations obtained from calibrated cameras to produce 3D pose by triangulation or pictorial structures model. More recently, many researchers (see refs. [10], [11]) used deep neural networks to model multi-view input with full 3D supervision.

Weak and self-supervision based methods for human pose estimation have been explored by many (see refs. [9], [30], [31], [42]) due to lack of 3D annotations. Pavlakos et al. (see ref. [30]) use a pictorial structures model to obtain a global pose configuration from the keypoint heatmaps of multi-view images. Nevertheless, their method needs full camera calibration and a keypoint detector producing 2D heatmaps.

Rhodin et al. (see ref. [31]) utilize multi-view consistency constraints to supervise a network. They need a small amount of 3D ground-truth data to avoid degenerate solutions where poses collapse to a single location. Thus, lack of in-the-wild 3D ground-truth data is a limiting factor for this method (see ref. [31]).

Recently introduced deep inverse graphics networks (see refs. [38], [45]) have been applied to the human pose estimation problem (see refs. [9], [42]). Tung et al. (see ref. [42]) train a generative adversarial network which has a 3D pose generator trained with a reconstruction loss between projections of predicted 3D poses and input 2D joints and a discriminator trained to distinguish predicted 3D pose from a set of ground truth 3D poses. Following this work, Drover et al. (see ref. [9]) eliminated the need for 3D ground-truth by modifying the discriminator to recognize plausible 2D projections.

To the best of our knowledge, Drover et al.'s method and the method of the present application described hereinafter are the only ones that do not require any 3D supervision or camera extrinsics. While Drover et al.'s method does not utilize image features, the method described in the present application makes use of both image features and epipolar geometry and produces much more accurate results (4.3 mm less error than Drover et al.'s method).

What is needed, therefore, is a three dimensional pose estimation system that is able to predict three dimensional (3D) human poses from a single image. Moreover, a three dimensional pose estimation system is needed that does not require any 3D supervision or camera extrinsics. Furthermore, a need exists for a three dimensional pose estimation system that creates its own 3D supervision by utilizing epipolar geometry and 2D ground-truth poses.

BRIEF SUMMARY OF EMBODIMENTS OF THE INVENTION

Accordingly, the present invention is directed to a system for estimating a three dimensional pose of one or more persons in a scene (i.e., a pose estimation system) that substantially obviates one or more problems resulting from the limitations and deficiencies of the related art.

In accordance with one or more embodiments of the present invention, there is provided a system for estimating a three dimensional pose of one or more persons in a scene, the system including one or more cameras, the one or more cameras configured to capture one or more images of the scene; and a data processor including at least one hardware component, the data processor configured to execute computer executable instructions. The computer executable instructions comprising instructions for: (i) receiving the one or more images of the scene from the one or more cameras; (ii) extracting features from the one or more images of the scene for providing inputs to a first branch pose estimation neural network; (iii) extracting features from the one or more images of the scene for providing inputs to a second branch pose estimation neural network; (iv) generating a first training signal from the second branch pose estimation neural network using a three dimensional reconstruction module for input into the first branch pose estimation neural network, the three dimensional reconstruction module generating an estimated three dimensional pose by performing triangulation on one or more two dimensional estimated poses generated by the second branch pose estimation neural network; (v) generating one or more volumetric heatmaps using the first branch pose estimation neural network; and (vi) applying a maximization function to the one or more volumetric heatmaps to obtain a three dimensional pose of one or more persons in the scene.

In a further embodiment of the present invention, during the training of the system, the data processor is further configured to execute computer executable instructions for: (vii) calculating the loss between one or more three dimensional poses generated by the first branch pose estimation neural network and the estimated three dimensional pose generated by the three dimensional reconstruction module using a loss function; and (viii) generating the first training signal for the first branch pose estimation neural network based upon the calculated loss.

In yet a further embodiment, the loss function utilized by the data processor comprises a smooth L1 loss function.

In still a further embodiment, the data processor is configured to extract the features from the one or more images of the scene using one or more residual networks followed by one or more deconvolution networks, which together form a shared backbone feature extractor for the first branch pose estimation neural network and the second branch pose estimation neural network.

In yet a further embodiment, during the training of the system, the data processor is further configured to execute computer executable instructions for: (vii) generating a second training signal from the first branch pose estimation neural network using a reprojection module for input into the second branch pose estimation neural network, the reprojection module comparing 3D-to-2D point projections generated based upon output from the first branch pose estimation neural network to the one or more two dimensional estimated poses generated by the second branch pose estimation neural network.

In still a further embodiment, during the training of the system, the data processor is further configured to execute computer executable instructions for: (vii) rigidly aligning, using the reprojection module, a plurality of three dimensional estimated poses generated by the first branch pose estimation neural network; (viii) calculating, using the reprojection module, a refined single three dimensional estimated pose as a weighted average of the plurality of rigidly aligned three dimensional estimated poses; and (ix) projecting, using the reprojection module, the refined single three dimensional estimated pose to a plurality of camera planes to create the 3D-to-2D point projections.

In yet a further embodiment, the first branch pose estimation neural network outputs estimated vertices of a canonical human mesh model.

In still a further embodiment, the second branch pose estimation neural network outputs an index UV map of image pixels where indexed UV values correspond to surface locations on the canonical human mesh model.

In yet a further embodiment, during the training of the system, the data processor is further configured to execute computer executable instructions for: (vii) comparing, using the three dimensional reconstruction module, the indexed UV values generated by the second branch pose estimation neural network, and generating a set of matching pairs of the indexed UV values that correspond to the same estimated vertex of the canonical human mesh model; (viii) for each pair in the set, calculating using the three dimensional reconstruction module, a 3D point in world coordinates using triangulation so as to form a calculated point set; and (ix) comparing the calculated point set with the estimated vertices generated from the first branch pose estimation neural network to generate the first training signal for the first branch pose estimation neural network.

In still a further embodiment, the maximization function applied to the one or more volumetric heatmaps by the data processor comprises a soft argmax function.

In yet a further embodiment, during the training of the system, the data processor is further configured to train the first branch pose estimation neural network while the second branch pose estimation neural network is kept frozen.

In still a further embodiment, during the training of the system, the data processor is further configured to train the second branch pose estimation neural network while the first branch pose estimation neural network is kept frozen.

It is to be understood that the foregoing summary and the following detailed description of the present invention are merely exemplary and explanatory in nature. As such, the foregoing summary and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which:

FIG. 8 illustrates triangulation results on the Human3.6M dataset in tabular form for the pose estimation system described herein (the effects of different 2D keypoint sources on triangulation performance are illustrated in the table);

FIG. 9 illustrates the results of the present model with different supervision types in comparison to recent state-of-the-art methods;

FIG. 10 illustrates the numerical performance results of the present model in comparison to the performance of weakly/self-supervised methods in the literature on the Human3.6M dataset;

FIG. 11 illustrates the fully supervised (FS) training results of the present model on the 3DHP dataset as a baseline;

DETAILED DESCRIPTION OF EMBODIMENTS OF THE INVENTION

Figure 1:
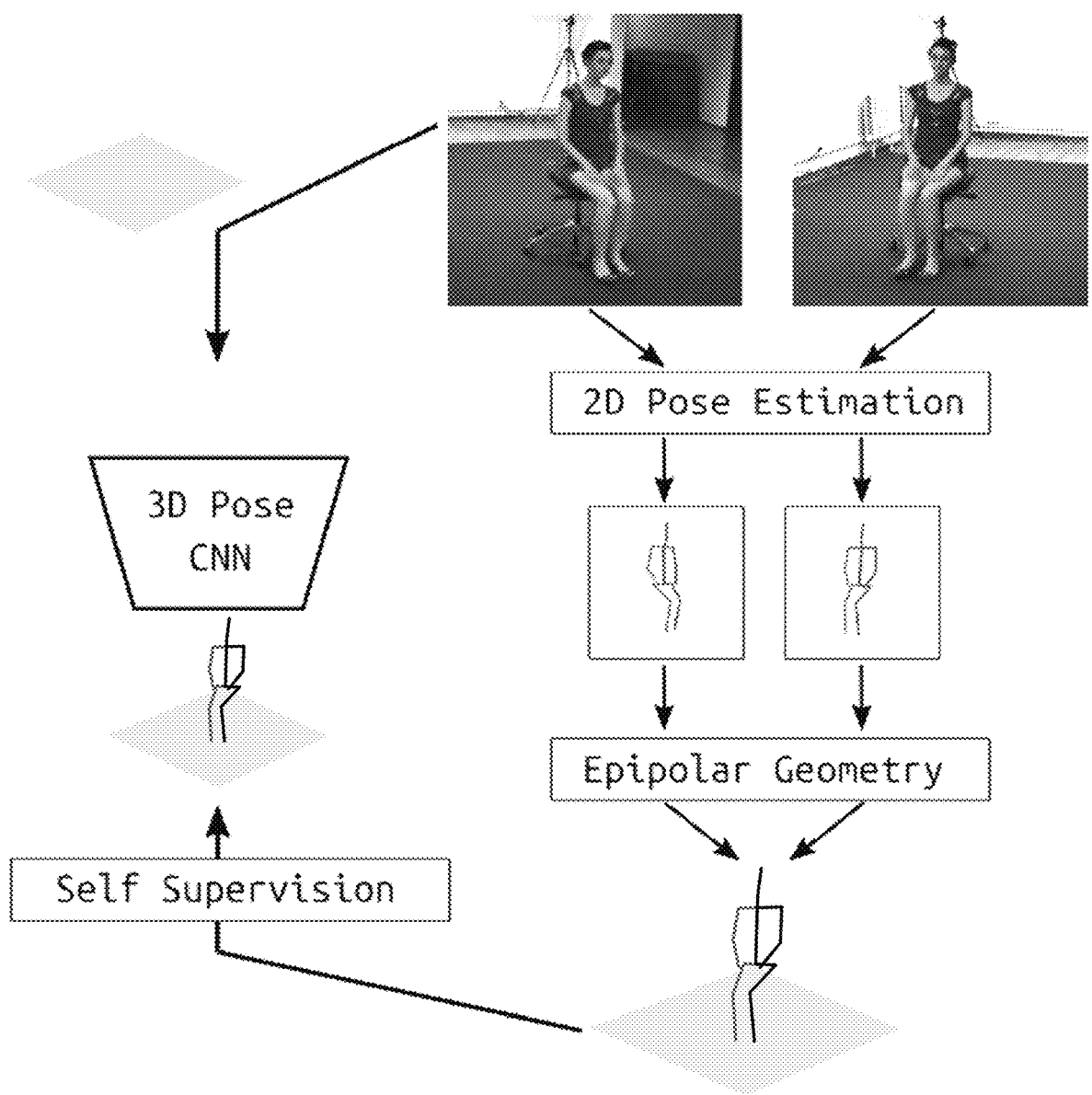
FIG. 1 is a schematic diagram of the functional aspects of the pose estimation system described herein, according to an illustrative embodiment of the invention.
Figure 2:
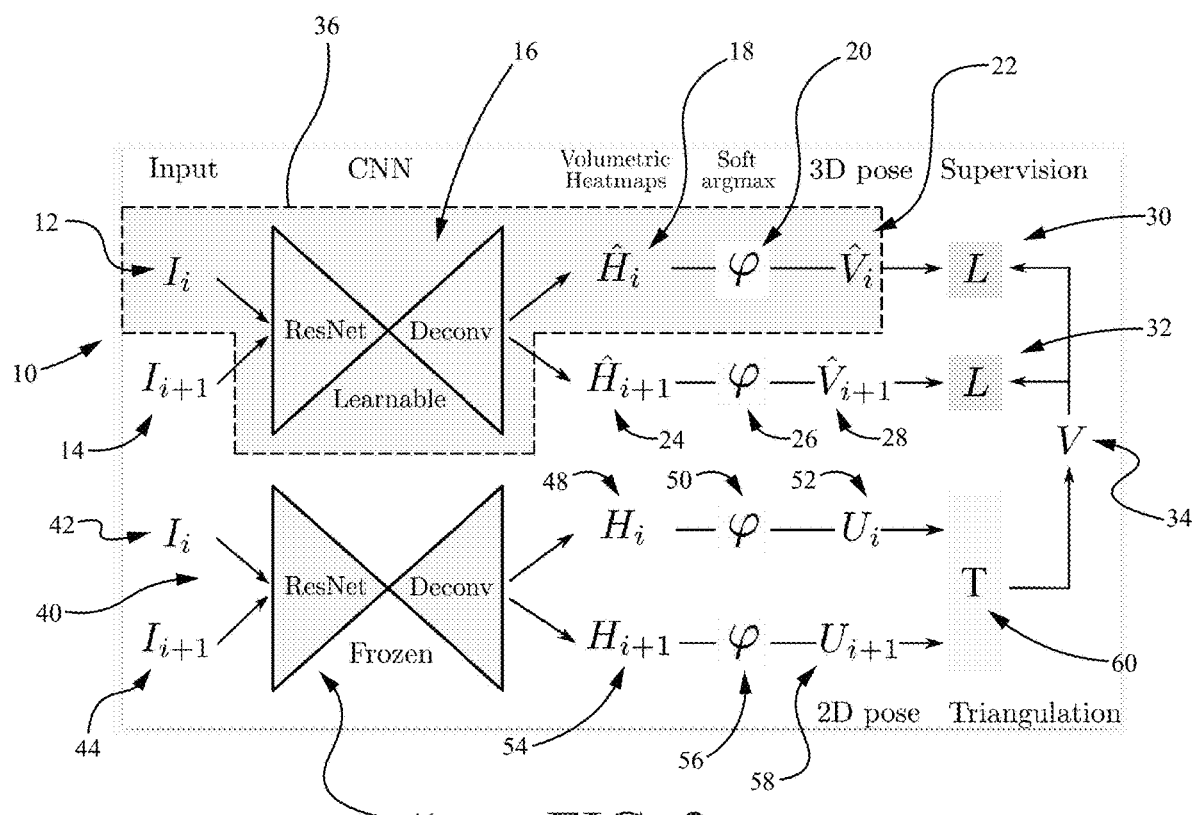
FIG. 2 is a schematic diagram of the overall architecture of the pose estimation system described herein during the training thereof, according to an illustrative embodiment of the invention.

As will be described hereinafter, a new system and method for three-dimensional (3D) pose estimation is disclosed. In addition, a system utilizing a plurality of cameras and a data processor for performing multi-person three-dimensional (3D) pose estimation is disclosed herein. The system and method described herein uses 2D pose estimation and epipolar geometry to obtain 3D poses, which are subsequently used to train a 3D pose estimator (see FIG. 1). The present system and method works with an arbitrary number of cameras (must be at least 2) and it does not need any 3D supervision or the extrinsic camera parameters, however, it can utilize them if provided. The present method is a single-view method during inference (i.e., using the system for pose estimation in practice); and a multi-view, self-supervised method during training. That is, only one camera is used during inference. On the Human3.6M (see ref. [16]) and MPI-INF-3DHP (see ref. [23]) datasets, the present system and method set the new state-of-the-art in 3D pose estimation for weakly/self-supervised methods. During the training of the system, both the upper and lower branches 10, 40 of the system (see FIG. 2) are active, whereas during inference, only the upper branch 40 of the system is active. In FIG. 2, the side "V" branch is the supervision signal.

Figure 4:
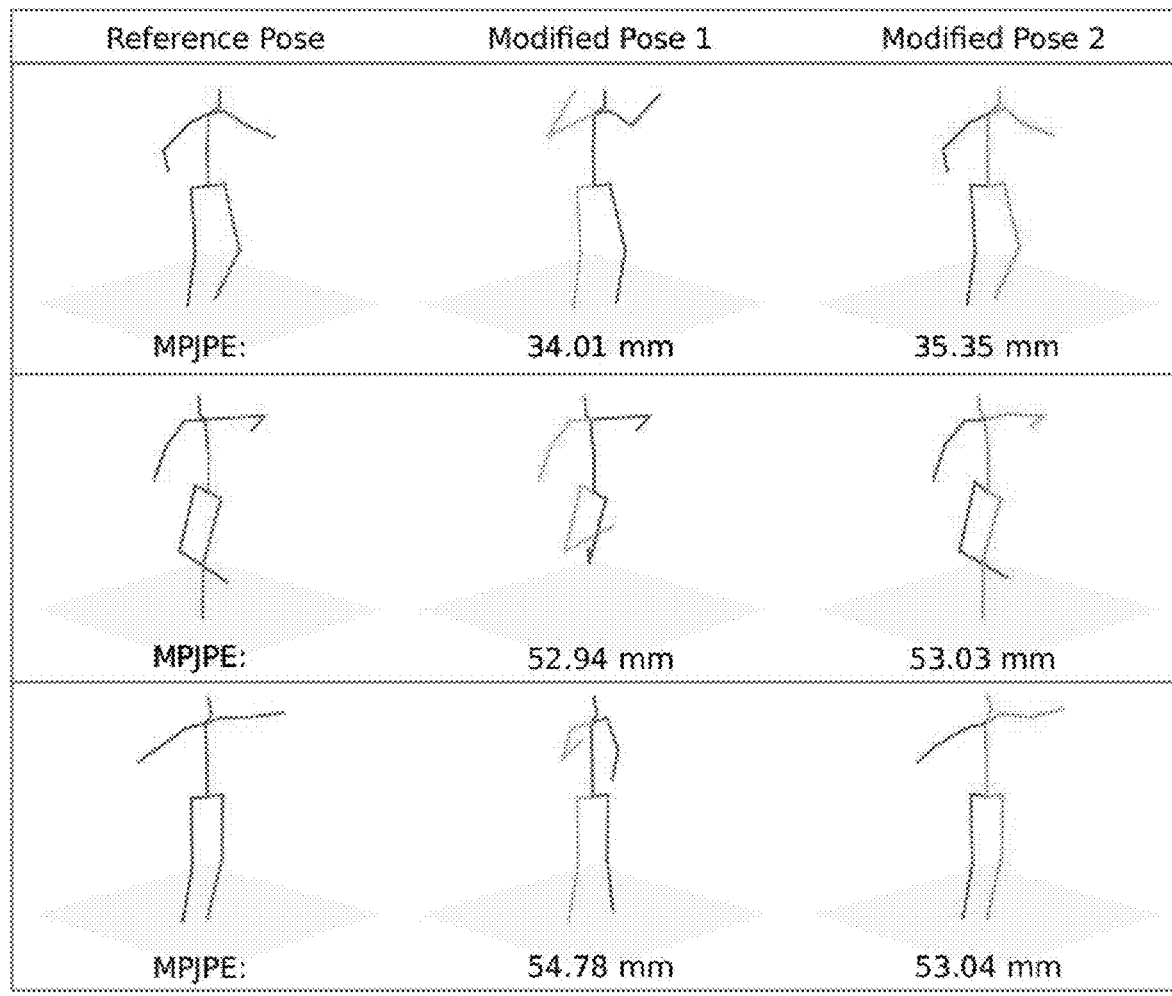
FIG. 4 illustrates reference poses from the Human3.6M dataset, according to an illustrative embodiment of the invention.

Human pose estimation allows for subsequent higher level reasoning, e.g., in autonomous systems (cars, industrial robots) and activity recognition. In such tasks, structural errors in pose might be more important than the localization error measured by the traditional evaluation metrics such as MPJPE (mean per joint position error) and PCK (percentage of correct keypoints). These metrics treat each joint independently, hence, fail to assess the whole pose as a structure. FIG. 4 shows that structurally very different poses yield the same MPJPE with respect to a reference pose. To address this issue, a new performance measure is introduced herein, called the Pose Structure Score (PSS), which is sensitive to structural errors in pose. PSS computes a scale invariant performance score with the capability to score the structural plausibility of a pose with respect to its ground truth. Note that PSS is not a loss function, it is a performance measure that can be used along with MPJPE and PCK to describe the representation capacity of a pose estimator. The Pose Structure Score (PSS) is a new metric used to determine the correctness of pose estimation models. Unlike conventional metrics that measure the distance between individual points and take an average, the overall pose structure is taken into account with PSS.

To compute PSS, the natural distribution of ground-truth poses first needs to be modeled. Ground truth poses are the reference. To this end, we use an unsupervised clustering method. Let p be the predicted pose for an image whose ground-truth is q. First, the cluster centers which are closest to p and q are found. If both of them are closest to (i.e., assigned to) the same cluster, then the pose structure score (PSS) of q is said to be 1, otherwise it is 0. In other words, if the ground truth pose and the estimated pose are assigned to the same cluster, then the score is 1, if not, then the score is zero.

1. System Architecture and Training

The overall training pipeline of the system and method described herein is illustrated in FIG. 2. The encircled dashed portion 36 in the upper branch of FIG. 2 denotes the inference pipeline. For training of the present system, the setup is assumed to be as follows. There are n cameras (n≥2 must hold) which simultaneously take the picture of the person in the scene. The cameras are given identification numbers from 1 to n where consecutive cameras are close to each other (i.e., they have a small baseline). The cameras produce images $I_1, I_2, \ldots I_n$. Then, the set of consecutive image pairs, $\{(I_i, I_{i+1})|i=1, 2, \ldots, n-1\}$, form the training examples. In the illustrative embodiment, during training, the present system is multi-view: a pair of images $(I_i, I_{i+1})$ simultaneously taken by two consecutive cameras is fed into the CNN pose estimators 16, 46. In particular, referring to FIG. 2, the images 12, 14 are fed into the CNN pose estimator 16 of the upper branch 10 during the training of the system, while the images 42, 44 are fed into the CNN pose estimator 46 of the lower branch 40 during the training of the system (image 12 is the same as image 42, and image 14 is the same as image 44). The present system is also self-supervised: the 3D pose (V) 34 generated by the lower branch 40 of the diagram in FIG. 2 using triangulation 60 (i.e., epipolar geometry) is used as a training signal for the CNN 16 in the upper branch 10 of the diagram. During inference (the encircled dashed part 36 of FIG. 2), the present method is a monocular method: it takes a single image ($I_i$) 12 as input and estimates the corresponding 3D pose ($\hat{V}_i$) 22. In FIG. 2, p represents the soft argmax function, T represents triangulation, and L represents smooth L1 loss. Specifically, with reference again to FIG. 2, during training, the CNN pose estimator 16 of the upper branch 10 outputs volumetric heatmaps 18, 24 ($\hat{H}_i$, $\hat{H}_{i+1}$) based on the respective input images 12, 14, while the CNN pose estimator 46 of the lower branch 40 outputs volumetric heatmaps 48, 54 ($H_i$, $H_{i+1}$) based on the respective input images 42, 44 (image 12 is the same as image 42, and image 14 is the same as image 44). A respective soft argmax activation function 20, 26 ($\varphi$) is applied to the volumetric heatmaps 18, 24 ($\hat{H}_i$, $\hat{H}_{i+1}$) in the upper branch 10, while a respective soft argmax activation function 50, 56 ($\varphi$) is applied to the volumetric heatmaps 48, 54 ($H_i$, $H_{i+1}$) in the lower branch 40. After applying the soft argmax activation functions 20, 26 ($\varphi$) to the respective volumetric heatmaps 18, 24 ($\hat{H}_i$, $\hat{H}_{i+1}$) in the upper branch 10, the respective 3D poses 22, 28 ($\hat{V}_i$, $\hat{V}_{i+1}$) are obtained. Similarly, after applying the soft argmax activation functions 50, 56 ($\varphi$) to the respective volumetric heatmaps 48, 54 ($H_i$, $H_{i+1}$) in the lower branch 40, the respective 2D poses 52, 58 ($U_i$, $U_{i+1}$) are obtained. Then, to obtain a 3D pose 34 (V) for corresponding synchronized 2D images, triangulation 60 is utilized. Finally, to calculate the loss between the 3D poses 22, 28 ($\hat{V}_i$, $\hat{V}_{i+1}$) predicted by the upper (3D) branch 10, the 3D pose 34 (V) determined from the lower branch 40 is projected onto corresponding camera space, then loss functions 30, 32 are used to train the upper (3D) branch 10. The loss functions 30, 32 are used to compare 3D poses 22, 28 ($\hat{V}_i$, $\hat{V}_{i+1}$) from the upper branch 10 to the 3D pose 34 (V) from the lower branch 40. The objective is to get the 3D poses 22, 28 ($\hat{V}_i$, $\hat{V}_{i+1}$) from the upper branch 10 as close as possible to the 3D pose 34 (V) from the lower branch 40 by means of using the minimization or loss functions 30, 32.

In the training pipeline of the present system (see FIG. 2), there are two branches 10, 40, each starting with the same pose estimation network 16, 46 (a ResNet followed by a deconvolution network (see ref. [36])). These networks 16, 46 were pre-trained on the MPII Human Pose dataset (MPII) (see ref. [2]). During training, only the pose estimation network 16 in the upper branch 10 is trained; the other one 46 is kept frozen. Because the pose estimation network 46 in the 2D lower branch 40 is kept frozen, the 2D lower branch 40 does not take any feedback from the 3D upper branch 10 (i.e., the 2D lower branch 40 is domain independent). During training, because the lower branch 40 is kept frozen, only weights in the upper branch 10 are learned. Weights are not determined for the lower branch 40. The upper branch 10 is the network that is being trained.

The present system can be trained using more than two (2) cameras, but for the sake of simplicity here, the training pipeline will be described for n=2. For n=2, each training example contains only one image pair. Images $I_i$ and $I_{i+1}$ are fed into both the 3D (upper) branch and 2D (lower) branch pose estimation networks to obtain volumetric heatmaps $\hat{H}$, $H \in R^{w \times h \times d}$ respectively, where w, h are the spatial size after deconvolution, d is the depth resolution defined as a hyper-parameter. After applying soft argmax activation function $\varphi(\cdot)$, the 3D pose $\hat{V} \in R^{J \times 3}$ and the 2D pose $U \in R^{J \times 2}$ outputs are obtained where J is the number of body joints. As such, the processing flow of the system occurs in the aforedescribed manner.

As an output of 2D pose branch, it is desired to obtain the 3D human pose V in the global coordinate frame. Let the 2D coordinate of the $j^{th}$ joint in the $i^{th}$ image be $U_{i,j}=[x_{i,j}, y_{i,j}]$ and its 3D coordinate be $[X_j, Y_j, Z_j]$, we can describe the relation between them assuming a pinhole image projection model:

$$\begin{bmatrix} x_{i,j} \\ y_{i,j} \\ w_{i,j} \end{bmatrix} = K[R \mid RT] \begin{bmatrix} X_j \\ Y_j \\ Z_j \\ 1 \end{bmatrix}, K = \begin{bmatrix} f_x & 0 & c_x \\ 0 & f_y & c_y \\ 0 & 0 & 1 \end{bmatrix}, T = \begin{bmatrix} T_x \\ T_y \\ T_z \end{bmatrix} \quad (1)$$

where $w_{i,j}$ is the depth of the $j^{th}$ joint in the $i^{th}$ camera's image with respect to the camera reference frame, K encodes the camera intrinsic parameters (e.g., focal length $f_x$ and $f_y$, principal point $c_x$ and $x_y$), R and T are camera extrinsic parameters of rotation and translation, respectively. Camera extrinsic parameters are used for transforming world coordinates into camera coordinates, whereas camera intrinsic parameters are used for transforming the camera coordinates into image coordinates. Camera distortion is omitted for simplicity. As such, the system performs two dimensional supervision in the aforedescribed manner.

When camera extrinsic parameters are not available, which is usually the case in dynamic capture environments, body joints can be used as calibration targets. The first camera is assumed to be the center of the coordinate system, which means R of the first camera is identity. For corresponding joints in $U_i$ and $U_{i+1}$, in the image plane, the fundamental matrix F is found satisfying $U_{i,j}FU_{i+1,j}=0$ for $\forall j$ using the RANSAC algorithm. From F, we calculate the essential matrix E by $E=K^TFK$. By decomposing E with SVD, four (4) possible solutions are obtained to R. The correct one was decided by verifying possible pose hypotheses by doing cheirality check. The cheirality check basically means that the triangulated 3D points should have positive depth (see ref. [26]). For example, if the left elbow is being considered in the first and second views, it is determined whether the elbow points in the first and second views correspond to the same elbow point.

Finally, to obtain a 3D pose V for corresponding synchronized 2D images, triangulation was utilized (i.e., epipolar geometry) as follows. For all joints in $(I_i, I_{i+1})$ that are not occluded in either image, triangulate a 3D point $[X_j, Y_j, Z_j]$ using polynomial triangulation (see ref. [13]). For settings including more than two (2) cameras, the vector-median is calculated to find the median 3D position. Triangulation is used for determining which two camera points correspond to the same 2D point in world coordinates. By following the aforedescribed methodology, the camera parameters are able to be obtained when the parameters are not available initially.

To calculate the loss between 3D pose in camera frame $\hat{V}$ predicted by the upper (3D) branch, V is projected onto corresponding camera space, then $\text{smooth}_{L_1}(V-\hat{V})$ is minimized to train the 3D branch where $$\text{smooth}_{L_1}(x) = \begin{cases} 0.5x^2, & \text{if } |x| < 1 \\ |x| - 0.5, & \text{otherwise} \end{cases} \quad (2)$$

The loss function is computed in the aforedescribed manner. The error between $\hat{V}$ from the upper branch and V from the lower branch is determined as described above.

In the illustrative embodiment of the system and method described herein, a frozen 2D pose estimator is utilized. In the training pipeline of the illustrative system and method, there are two branches each of which is starting with a pose estimator. While the estimator in the upper branch is trainable, the other one in the lower branch is frozen. The job of the lower branch estimator is to produce 2D poses. One might question the necessity of the frozen estimator since 2D poses could be obtained from the trainable upper branch as well. When such an attempt was made, the method produced degenerate solutions where all keypoints collapse to a single location. In fact, other multi-view methods have faced the same problem (see refs. [31, 37]). Rhodin et al. (see ref. [31]) solved this problem by using a small set of ground-truth examples, however, obtaining such ground-truth may not be feasible in most of the "in the wild" settings. Another solution proposed recently (see ref. [37]) is to minimize angular distance between estimated relative rotation $\hat{R}$ (computed via Procrustes alignment of the two sets of keypoints) and the ground truth R. Nevertheless, it is hard to obtain ground truth R in dynamic capture setups. To overcome these shortcomings, we utilize a frozen 2D pose detector during training time only.

2. Inference

Inference involves the encircled dashed portion 36 in FIG. 2. The input is just a single image and the output is the estimated 3D pose $\hat{V}$ obtained by a soft-argmax activation, $\varphi(\cdot)$, on 3D volumetric heatmap $\hat{H}_i$. During inference, the present system is able to obtain a pose from a single RGB image.

3. Refinement

Figure 3:
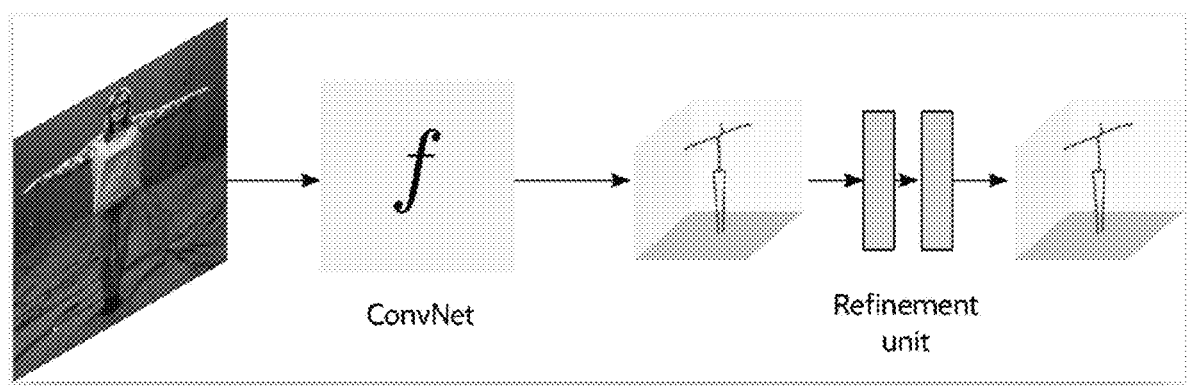
FIG. 3 is a schematic diagram of the overall interference pipeline with a refinement unit of the pose estimation system described herein, according to an illustrative embodiment of the invention.

In the literature, there are several techniques (see refs. [12, 22, 40]) to lift detected 2D keypoints into 3D joints. These methods are capable of learning generalized 2D→3D mapping which can be obtained from motion capture (MoCap) data by simulating random camera projections. Integrating a refinement unit (RU) to the self-supervised model described herein can further improve the pose estimation accuracy. In this way, one can train the model on his/her own data which consists of multiple view footages without any labels and integrate it with RU to further improve the results. To make this possible, the input layer of RU is modified to accept noisy 3D detections from the model and make it learn a refinement strategy (see FIG. 3). FIG. 3 illustrates an overall inference pipeline with a refinement unit which is an optional stage to refine the predictions of the model trained with self-supervision. The f function denotes the inference function (the encircled dashed portion 36 in FIG. 2) of the present system. The refinement routine of the system refines the estimated 3D pose, and makes it better. The output of inference, namely $\hat{V}_i$ from the upper branch 10, is the input to the refinement routine. As shown in FIG. 3, the refinement unit is inserted after $\hat{V}_i$ from the upper branch 10. As such, refinement is a post-processing routine during inference.

The overall RU architecture is inspired by references [12, 22]. It has two (2) computation blocks which have certain linear layers followed by Batch Normalization (see ref. [15]), Leaky ReLU (see ref. [21]) activation and Dropout layers to map 3D noisy inputs to more reliable 3D pose predictions. To facilitate information flow between layers, residual connections are added (see ref. [14]) and apply intermediate loss to expedite the intermediate layers' access to supervision.

4. Pose Structure Score

As we discussed above, traditional evaluation metrics (such as MPJPE, PCK) treat each joint independently, hence, fail to assess the whole pose as a structure. In FIG. 4, we present example poses that have the same MPJPE but are structurally very different, with respect to a reference pose. More specifically, on the left side of FIG. 4, reference poses from Human3.6M dataset are depicted. In the middle of FIG. 4, manually modified poses are depicted. The poses in the middle of FIG. 4 have been modified to obtain similar MPJPE with poses on the right side of FIG. 4, yet they are structured different from reference poses. The poses on the right side of FIG. 4 are obtained by adding random gaussian noise to each of the body joints.

In the illustrative embodiment, a new performance measure, called the Pose Structure Score (PSS), is utilized that is sensitive to structural errors in pose. PSS computes a scale invariant performance score with the capability to assess the structural plausibility of a pose with respect to its ground truth pair. Note that PSS is not a loss function, it is a performance score that can be used along with MPJPE and PCK to describe the representation capacity of a pose estimator. PSS is an indicator about the deviation from the ground truth pose that has the potential to cause a wrong inference in a subsequent task requiring semantically meaningful poses, e.g., action recognition, human-robot interaction.

Now, the manner in which PSS is obtained will be described. Given a ground-truth set composed of n poses $p_i$, $i \in \{1, \ldots n\}$, each pose is normalized by $$\hat{p}_i = \frac{p_i}{\|p_i\|}.$$

Then, compute k cluster centers $\mu_j$, $\in \{1, \ldots, k\}$ are computed using k-means clustering. Then, to compute the PSS of a predicted pose p against its ground-truth pose q, we use $$PSS(p, q) = \delta(C(p), C(q)) \text{ where} \quad (3)$$

-continued $$C(p) = \underset{k}{\operatorname{argmin}} \|p - \mu_k\|_2^2, \quad \delta(i, j) = \begin{cases} 1, & \text{if } i = j \\ 0, & \text{if } i \neq j \end{cases} \quad (4)$$

Figure 5:
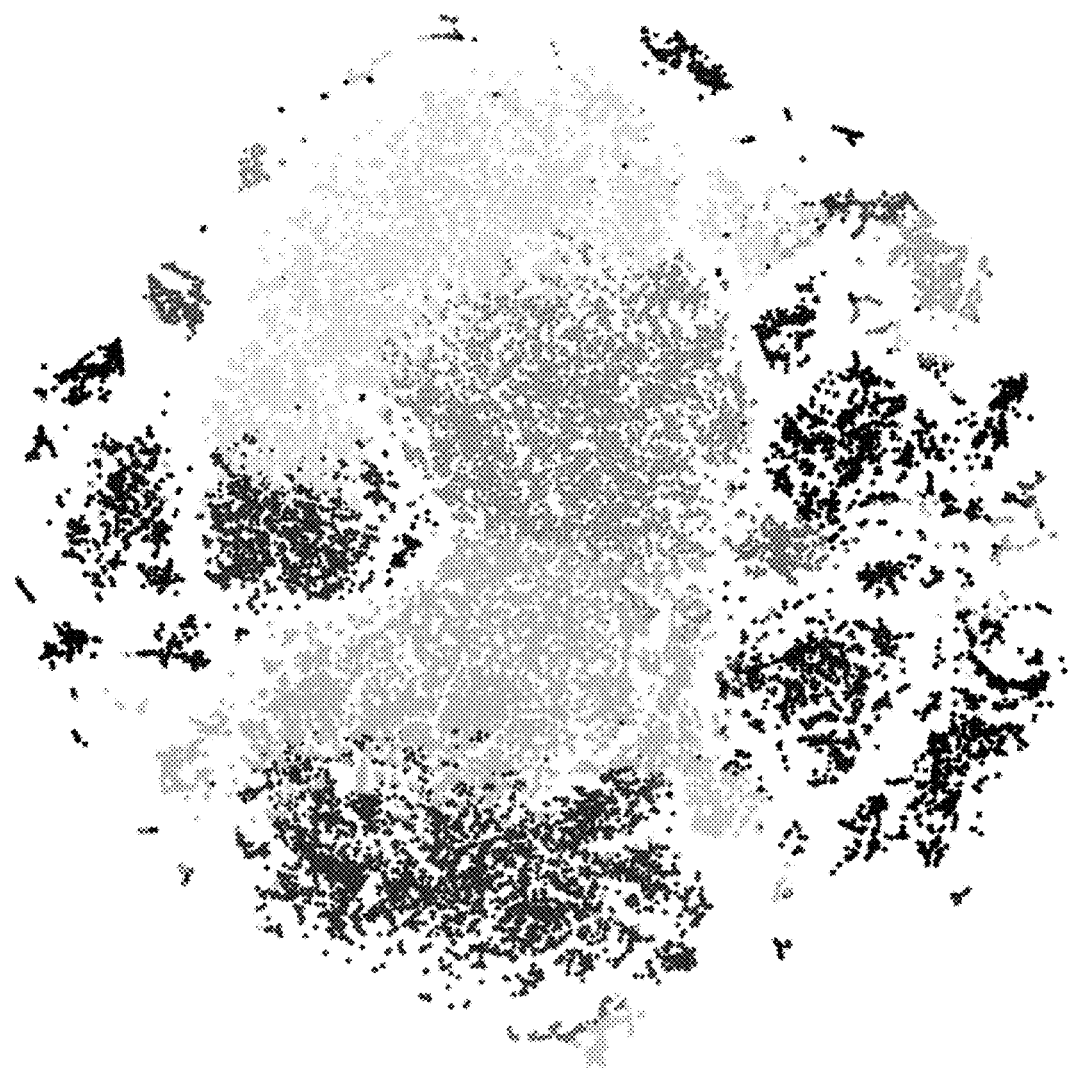
FIG. 5 illustrates a t-SNE graph of human poses after clustering (k=10), according to an illustrative embodiment of the invention.
Figure 6:
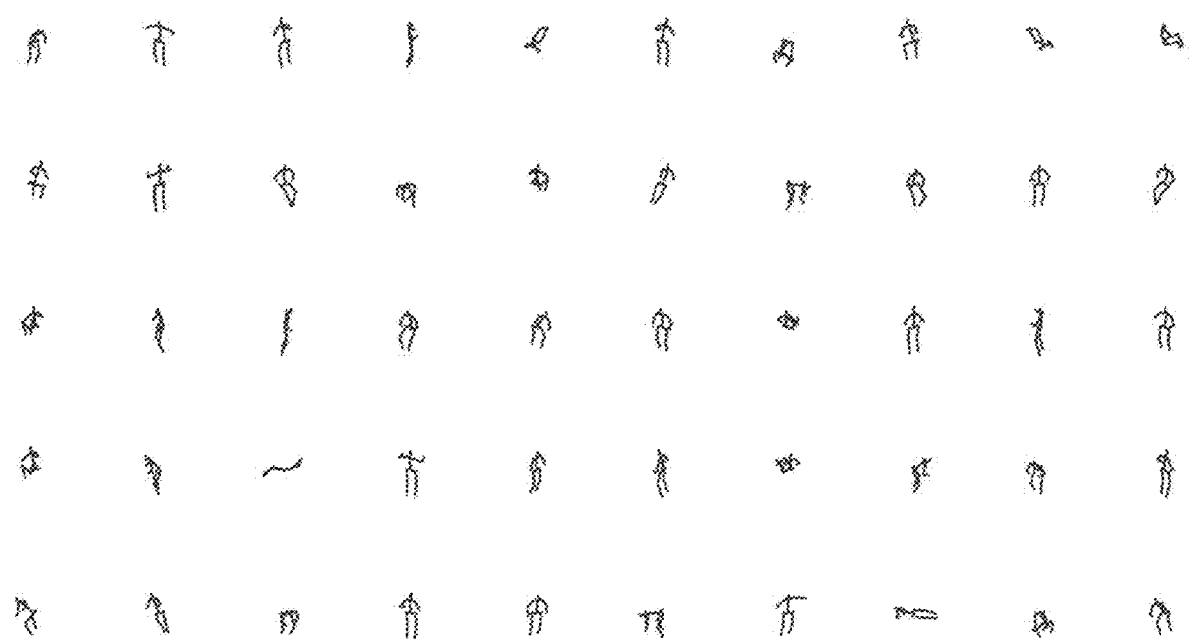
FIG. 6 illustrates cluster centers which represent the canonical poses in Human3.6M (k=50), according to an illustrative embodiment of the invention.

The PSS of a set of poses is the average over their individual scores as computed in equation (3) above. FIG. 5 shows the t-SNE (see ref. [43]) graph of poses and clusters. In FIG. 5, k=10 was chosen for visualization purposes. The different grayscale shades in FIG. 5 represent different clusters. FIG. 6 depicts the cluster centers which represent canonical poses in Human3.6M dataset (k=50).

In the experiments performed using the present method, the number of pose clusters were chosen as 50 and 100. The corresponding PSS results were denoted with PSS@50 and PSS@100 expressions. Note that PSS computes the percentage of correct poses, therefore higher scores are better.

Next, the implementation details of the illustrative method and system will be described. The Integral Pose (see ref. [36]) architecture was used for both 2D and 3D branches with a ResNet-50 (see ref. [14]) backend. Input image and output heatmap sizes are 256×256 and J×64×64×64, respectively where J is the number of joints. All models used in experiments were initialized after training on the MPII (see ref. [2]).

During training, mini-batches of size 32 were used, each one containing $I_i$, $I_{i+1}$ image pairs. If more than two cameras are available, the views from all cameras are included in a mini-batch. The network is trained for 140 epochs using Adam optimizer (see ref. [17]) with a learning rate of $10^{-3}$ multiplied with 0.1 at steps 90 and 120. Training data is augmented by random rotations of ±30° and scaled by a factor between 0.8 and 1.2. Additionally, synthetic occlusions (see ref. [34]) are utilized to make the network robust to occluded joints. For the sake of simplicity, we run the 2D branch once to produce triangulated 3D targets and train the 3D branch using cached labels. The whole pipeline was implemented using PyTorch (see ref. [27]).

5. Experiments

With regard to datasets, experiments were first conducted on the Human3.6M (H36M) large scale 3D human pose estimation benchmark (see ref. [16]). It is one of the largest datasets for 3D human pose estimation with 3.6 million images featuring 11 actors performing 15 daily activities, such as eating, sitting, walking and taking a photo, from four (4) camera views. This dataset was mainly used for both quantitative and qualitative evaluation.

The standard protocol was followed on H36M and the subjects 1, 5, 6, 7, 8 were used for training and the subjects 9, 11 were used for evaluation. Evaluation is performed on every $64^{th}$ frame of the test set. Average errors were included for each method.

To demonstrate the further applicability of the method described herein, MPI-INF-3DHP (3DHP) was used (see ref. [23]) which is a recent dataset that includes both indoor and outdoor scenes. The standard protocol was followed: the five chest-height cameras and the provided 17 joints (compatible with H36M) were used for training. For evaluation, the official test set was used, which includes challenging outdoor scenes. The results were reported in terms of PCK and NPCK to be consistent with reference [31]. Note no kind of background augmentation was utilized to boost the performance for outdoor test scenes.

With respect to metrics, pose accuracy was evaluated in terms of MPJPE (mean per joint position error), PMPJPE (procrustes aligned mean per joint position error), PCK (percentage of correct keypoints), and PSS at scales @50 and @100. To compare the present model with reference [31], the normalized metrics NMPJPE and NPCK were measured; refer to reference [31] for further details. Note that PSS, by default, uses normalized poses during evaluation. In the presented results "n/a" means "not applicable" where it is not possible to measure respective metric with provided information, "-" means "not available". For instance, it is not possible to measure MPJPE or PCK when R, the camera rotation matrix, is not available. For some of the previous methods with open source code, their respective PSS scores were indicated. In the future, it is hoped that PSS will be adapted as an additional performance measure, thus more results will become available for complete comparisons.

6. Experimental Results

Table 1 of FIG. 8 summarizes triangulation results from different 2D keypoint sources on the H36M dataset. This table depicts the effects of different 2D keypoint sources on triangulation performance. In Table 1, GT 2D denotes the usage of ground truth 2D labels. Also, in this table, H36M 2D and MPII 2D shows the pose estimation models trained on those datasets. Note that training subjects were used to obtain these results in Table 1, since the goal was to find out the performance of triangulation on the training data. Overall, the quality of estimated keypoints is crucial to attain better results. When the ground truth 2D keypoints and camera geometry are available, triangulation gives 4.3 mm error and 99% PSS which is near perfect. Lack of camera geometry reduces the PMPJPE and PSS@50 by a small amount of 13 mm and 1%, respectively. A pose detector trained on the 2D labels of H36M improves the MPII-pretrained one up to 17 mm and 5%. Note that, it is expected to have slightly worse performance when evaluating the MPII-pretrained detector on the H36M validation set. Data in H36M was captured with markers, and therefore, have high accuracy and consistency in 2D annotations across subject and scenes; on the other hand, the annotations in MPII were done by humans and some of the keypoints are localized differently. For instance, shoulders and hips are closer to edges of the body in the MPII dataset.

Figure 7:
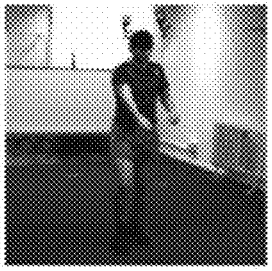
FIG. 7 illustrates qualitative results on the Human3.6M dataset, according to an illustrative embodiment of the invention.

Qualitative results on the Human3.6M dataset are depicted in FIG. 7. In the results illustrated in FIG. 7, 3D poses are provided from different camera views for better visualization. The last row in FIG. 7 depicts a failure case. In FIG. 7, FS denotes fully supervised training, and SS denotes self-supervised training.

Compared to Pavlakos et al.'s results (see ref. [30]), the triangulation performed in conjunction with the present system and method using an MPII-pretrained detector is 11 mm better in terms of MPJPE.

In Table 2 of FIG. 9, the results of the model described herein are presented with different supervision types in comparison with recent state-of-the-art methods. The top part of Table 2 presents a comparison of results between the present methods trained with different settings and the state-of-the-art fully supervised methods using ground truth data. In Table 2, FS denotes fully supervised, and SS denotes self-supervised. The bottom part of Table 2 presents the effect of adding refinement unit (RU) over SS (* uses the 2D keypoints from an MPII pre trained model as input, hence is comparable to the present SS+RU model). The fully supervised (FS) version of our model is presented to provide a baseline. The implementation of "Integral Pose" architecture (see ref. [36]) in conjunction with the present system and method produced a slightly different result than reported. The difference between the result (52 mm) obtained herein and the reported one (see ref. [36]) (49 mm) can be attributed to the authors' 2D-3D mixed training, which was not performed in conjunction with the present system and method so that the 3D pose estimation stage was decoupled from 2D.

The self-supervised (SS) model described herein performs quite well compared to the recent fully 3D supervised methods (see refs. [29, 32, 33, 41]), which require abundant labeled data to learn. Obtaining comparable results to state-of-the-art methods without using any 3D ground truth examples is a promising step for such a nontrivial task.

Refinement Unit (RU), which is an optional extension to the present SS network, is helpful for achieving better results. Adding RU further improves the performance of our SS model by 20%. To measure the representation capacity of the outputs from the present SS model, its result were compared with Martinez et al.'s work (see ref. [22]). Since the RU architecture is identical to Martinez et al., their model trained with 2D keypoints was selected from an MPII-pretrained pose detector for a fair comparison. These results show that 3D depth information learned by the present SS training method provides helpful cues to improve the performance of 2D-3D lifting approaches.

In the top part of Table 4 in FIG. 11, the FS training results are shown on the 3DHP dataset as a baseline. That information is further used to analyze the differences between FS and SS training. The top part of Table 4 depicts fully supervised training results. The middle part of Table 4 depicts results from self-supervised learning using only subject 1. The bottom part of Table 4 depicts results from self-supervised training without any ground truth examples.

Table 3 of FIG. 10 outlines the performance of weakly/self-supervised methods in the literature along with the present method on the H36M dataset. The top part of Table 3 includes the methods not requiring paired 3D supervision. That is, the top part of Table 3 contains results for methods that can be trained without 3D ground truth labels (Tung et al. (see ref. [42]) uses unpaired 3D supervision which is easier to get. 3DInterp denotes the results of ref. [45] implemented by ref. [42]. 2D GT denotes training with triangulations obtained from ground truth 2D labels). Since Tung et al. (see ref. [42]) used unpaired 3D ground truth labels that are easier to obtain, the Tung results were placed in the top part of Table 3. The present SS model (with or without R) outperforms all previous methods (see refs. [30, 42]) by a large margin in MPJPE metric. A large difference (21 mm) was observed between training with ground truth 2D triangulations and MPII-pretrained ones. This gap indicates that the 2D keypoint estimation quality is crucial for better performance. In the middle part of Table 3, results from methods requiring a small set of ground truth data are presented (S1 denotes using ground truth labels of H36M subject #1 during training).

To better understand the source of performance gain in the present method and Rhodin et al.'s method (see ref. [31]), the gap between the models trained with full supervision (FS) and subject 1 of H36M and 3DHP only (S1) can be analyzed. In the present method, the difference between FS and S1 training is 12 and 9 mm, while Rhodin et al.'s difference is 15 and 18 mm for H36M and 3DHP, respectively (lower is better). These results demonstrate that the present learning strategy is better at closing the gap. Even though Rhodin et al. uses S1 for training, the present SS method outperformed it on the H36M dataset. In the case of S1 training, there is an explicit improvement (14 mm, 4 mm for H36M and 3DHP respectively) with the present approach. In addition, SS training with the present method on 3DHP has comparable results to Rhodin et al.'s S1.

Finally, the bottom part of Table 3 in FIG. 10 gives a fair comparison of the present model against Drover et al.'s model (see ref. [9]) since they report results only with 14 joints. The present method yields 4 mm less error than their approach.

Unlike Drover et al.'s method, which takes a two dimensional pose as an input, the method described in the present application takes an image as an input. During training, the method described in the present application uses multi-view images (i.e. images of the same scene taken from different cameras) and multi-view geometry. By contrast, the method in Drover et al. does not use multi-view images or multi-view geometry. Also, Drover et al. does not employ self-supervision, rather the training used in Drover et al. method is considered weak supervision (or unpaired supervision, particularly). Moreover, unlike the method in Drover et al., the method described in the present application does not use image features to check whether a 2D prediction is realistic. Further, the method described in the present application does not use adversarial learning to determine if the poses are realistic, and the method in the present application does not rely on a database of 2D poses.

The method described in the present application employs self-supervision. The present method is not trained using two dimensional ground truth data. Also, the present method does not need a set of 3D ground truth labels. The present method uses triangulation to create a self-supervised signal. Unlike previous methods, the present method performs training with triangulated two dimensional keypoints obtained from a two dimensional pose estimator.

7. Biomechanical System Applications

Figure 12:
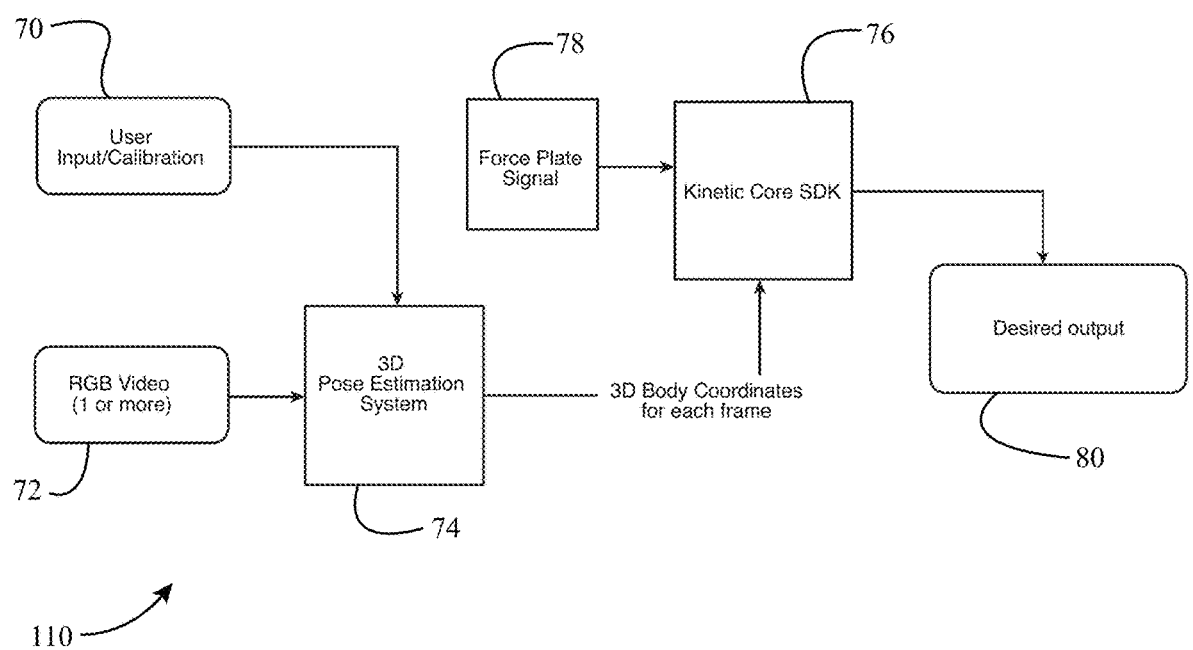
FIG. 12 is a schematic diagram of a first illustrative embodiment of biomechanical analysis system.

Now, with reference to the block diagrams in FIGS. 12-16, several illustrative biomechanical analysis systems in which the aforedescribed pose estimation system can be utilized will be explained. Initially, in the block diagram 110 of FIG. 12, it can be seen that the 3D pose estimation system 74 receives images of a scene from one or more RGB video cameras 72. The 3D pose estimation system 74 extracts the features from the images of the scene for providing inputs to a convolutional neural network. Then, the 3D pose estimation system 74 generates one or more volumetric heatmaps using the convolutional neural network, and applies a maximization function to the one or more volumetric heatmaps in order to obtain a three dimensional pose of one or more persons in the scene. As shown in FIG. 12, the 3D pose estimation system 74 determines one or more three dimensional coordinates of the one or more persons in the scene for each image frame, and outputs the three dimensional coordinates to a kinetic core software development kit (SDK). In addition, as shown in FIG. 12, user input and/or calibration parameters 70 may also be received as inputs to the 3D pose estimation system 74.

In the illustrative embodiment of FIG. 12, in addition to the three dimensional coordinates for each image frame from the 3D pose estimation system 74, the kinetic core SDK 76 may also receive one or more force plate signals 78 from a force plate as inputs. Then, the kinetic core SDK 76 determines and outputs one or more biomechanical performance parameters 80 using the three dimensional coordinates from the 3D pose estimation system 74 and the one or more force plate signals from the force plate. The illustrative biomechanical analysis system of FIG. 12 does not include trained CNN backpropagation, but another illustrative biomechanical analysis system that will be described hereinafter does include trained CNN backpropagation.

Figure 13:
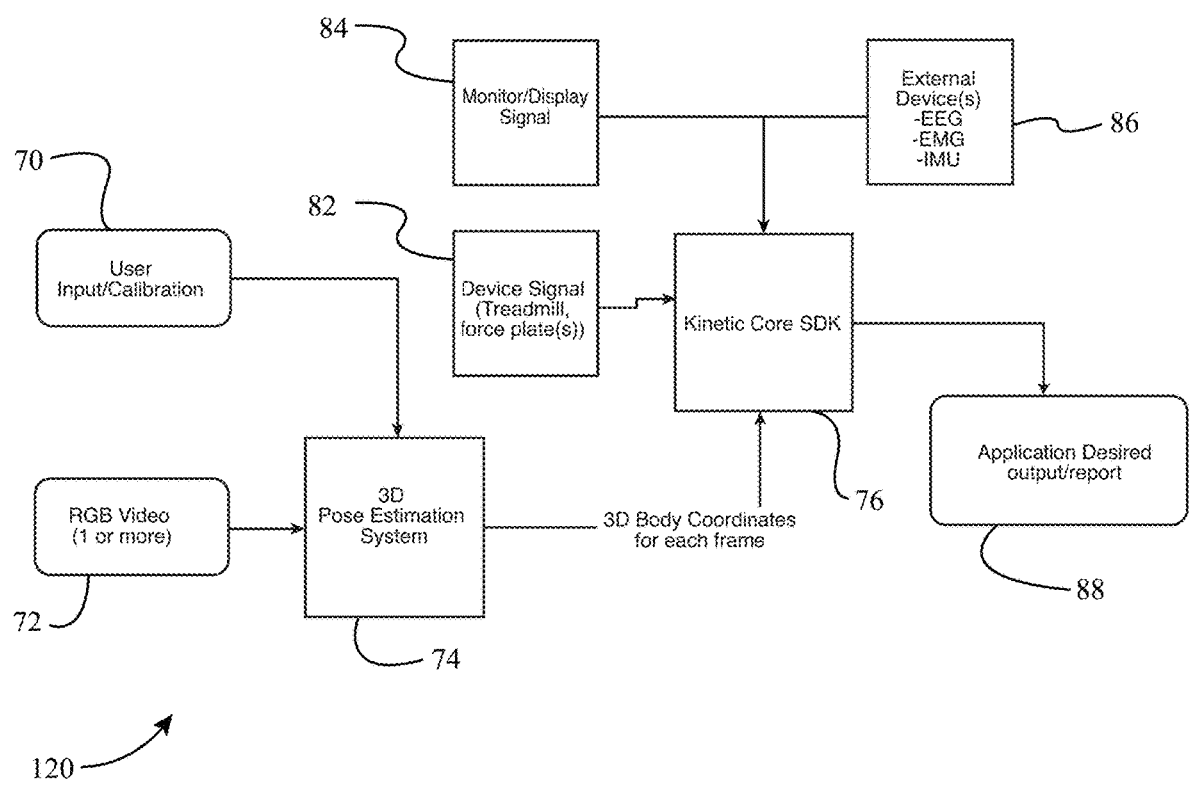
FIG. 13 is a schematic diagram of a second illustrative embodiment of biomechanical analysis system.

Next, referring to FIG. 13, a second illustrative biomechanical analysis system in which the pose estimation system may be utilized will be described. With reference to the block diagram 120 of FIG. 13, it can be seen that the second illustrative biomechanical analysis system is similar in many respects to the first illustrative biomechanical analysis system described above. As such, for the sake of brevity, the features that the second illustrative biomechanical analysis system has in common with the first illustrative biomechanical analysis system will not be discussed because these features have already been explained above. Although, unlike the first illustrative biomechanical analysis system, the second illustrative biomechanical analysis system of FIG. 13 has several different inputs to the kinetic core SDK 76. More specifically, in the illustrative embodiment of FIG. 13, in addition to the three dimensional coordinates for each image frame from the 3D pose estimation system 74, the kinetic core SDK 76 may also receive one or more device signals 82 from an instrumented treadmill and/or one or more force plates as inputs. For example, the instrumented treadmill and the one or more force plates may be similar to those described in U.S. Pat. No. 10,646,153, the entire disclosure of which is incorporated herein by reference. In addition, as shown in FIG. 13, the kinetic core SDK 76 may receive a monitor/display signal 84 as an input (e.g., an input signal from a touchscreen display). Further, as shown in FIG. 13, the kinetic core SDK 76 may receive one or more signals 86 from one or more other external devices, such as an electroencephalogram (EEG) device, an electromyography (EMG) device, and/or one or more inertial measurement units (IMUs). Then, the kinetic core SDK 76 determines and outputs one or more biomechanical performance parameters in an application desired output/report 88 using the three dimensional coordinates from the 3D pose estimation system 74 and the one or more signals 82, 84, 86 from the connected devices.

Figure 14:
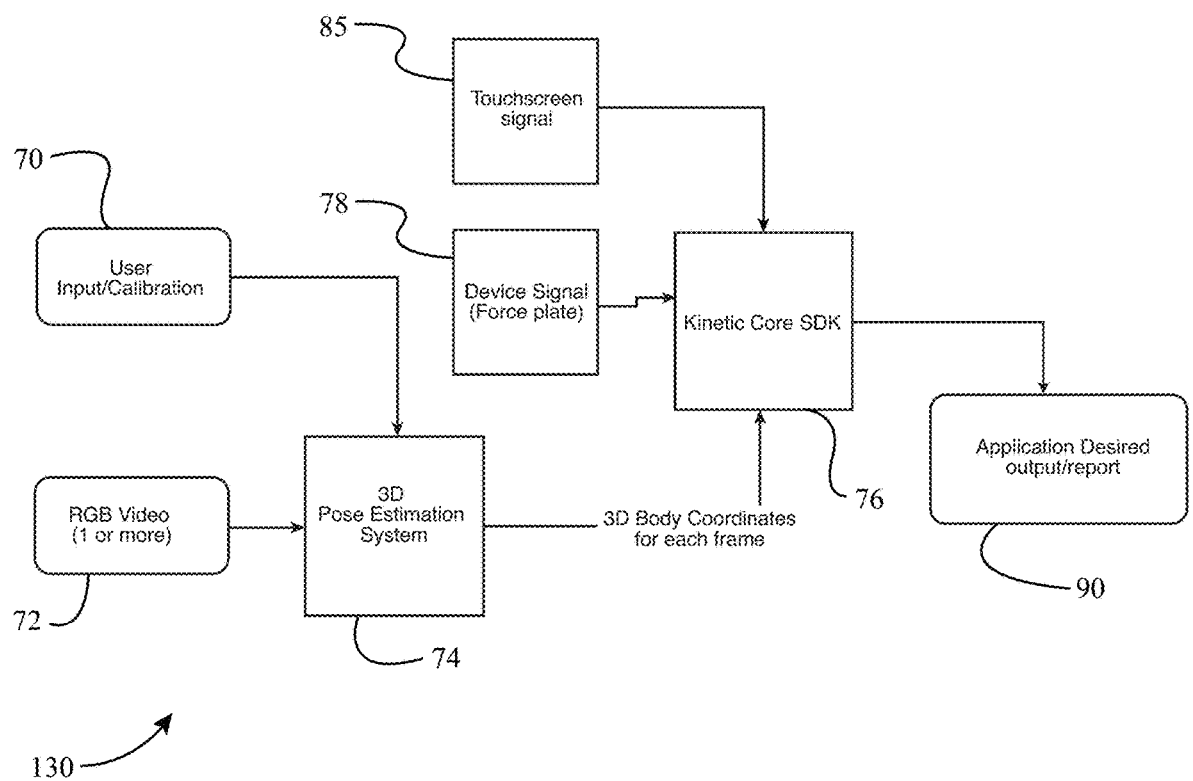
FIG. 14 is a schematic diagram of a third illustrative embodiment of biomechanical analysis system.

Next, referring to FIG. 14, a third illustrative biomechanical analysis system in which the pose estimation system may be utilized will be explained. With reference to the block diagram 130 of FIG. 14, it can be seen that the third illustrative biomechanical analysis system is similar in many respects to the first and second illustrative biomechanical analysis systems described above. As such, for the sake of brevity, the features that the third illustrative biomechanical analysis system has in common with the first and second illustrative biomechanical analysis systems will not be discussed because these features have already been explained above. Although, unlike the first illustrative biomechanical analysis system, the third illustrative biomechanical analysis system of FIG. 14 has several different inputs to the kinetic core SDK 76. More specifically, in the illustrative embodiment of FIG. 14, in addition to the three dimensional coordinates for each image frame from the 3D pose estimation system 74, the kinetic core SDK 76 may receive a touchscreen signal 85 as an input from a touchscreen device (e.g., an input signal from a touchscreen display). In addition, as shown in FIG. 14, the kinetic core SDK 76 may also receive one or more force plate signals 78 from a force plate as inputs. Then, the kinetic core SDK 76 determines and outputs one or more biomechanical performance parameters in an application desired output/report 90 using the three dimensional coordinates from the 3D pose estimation system 74 and the signals 78, 85 from the connected devices.

Now, referring to FIG. 15, a fourth illustrative biomechanical analysis system in which the pose estimation system may be utilized will be described. With reference to the block diagram 140 of FIG. 15, it can be seen that the fourth illustrative biomechanical analysis system is similar in many respects to the preceding illustrative biomechanical analysis systems described above. As such, for the sake of brevity, the features that the fourth illustrative biomechanical analysis system has in common with the first, second, and third illustrative biomechanical analysis systems will not be discussed because these features have already been explained above. Although, unlike the preceding illustrative biomechanical analysis systems, the fourth illustrative biomechanical analysis system of FIG. 15 includes trained CNN backpropagation. More specifically, in the illustrative embodiment of FIG. 15, the kinetic core SDK 76 is operatively coupled to one or more trained convolutional neural networks (CNNs) 75, which in turn, are operatively coupled to the 3D pose estimation system 74 so that better accuracy may be obtained from the 3D pose estimation system 74. In the illustrative embodiment of FIG. 15, in addition to the three dimensional coordinates for each image frame from the 3D pose estimation system 74, the kinetic core SDK 76 receives an external device signal 78 from an external device, such as a force plate. Then, the kinetic core SDK 76 determines and outputs one or more biomechanical performance parameters in a biomechanical output report 92 using the three dimensional coordinates from the 3D pose estimation system 74 and the signal 78 from the connected external device. As shown in FIG. 12, the biomechanical output report 92 may include annotated datasets and/or kinematic and kinetic profiles for the one or more persons in the scene.

Figure 16:
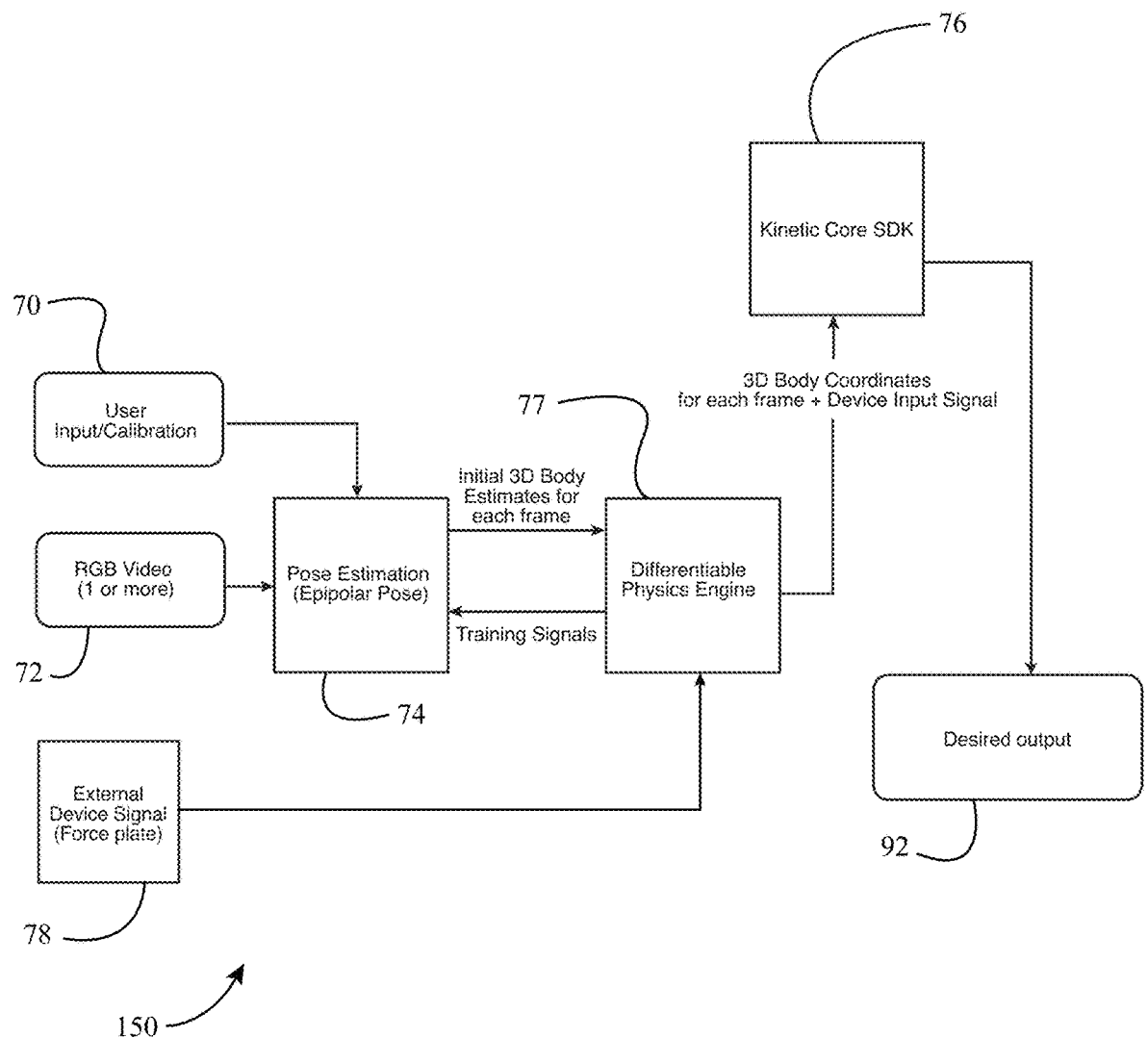
FIG. 16 is a schematic diagram of a fifth illustrative embodiment of biomechanical analysis system.

Finally, referring to FIG. 16, a fifth illustrative biomechanical analysis system in which the pose estimation system may be utilized will be described. With reference to the block diagram 150 of FIG. 16, it can be seen that the fifth illustrative biomechanical analysis system is similar in many respects to the preceding illustrative biomechanical analysis systems described above. As such, for the sake of brevity, the features that the fifth illustrative biomechanical analysis system has in common with the first, second, third, and fourth illustrative biomechanical analysis systems will not be discussed because these features have already been explained above. Although, unlike the preceding illustrative biomechanical analysis systems, the fifth illustrative biomechanical analysis system of FIG. 16 includes a differentiable physics engine 77. More specifically, in the illustrative embodiment of FIG. 16, the differentiable physics engine 77 operatively couples the kinetic core SDK 76 to the 3D pose estimation system 74 and the external device signal 78 from an external device, such as a force plate. As shown in FIG. 16, the differentiable physics engine 77 receives initial 3D body estimates for each image frame from the 3D pose estimation system 74, and then sends training signals to the 3D pose estimation system 74 so that better accuracy may be obtained from the 3D pose estimation system 74. After receiving the 3D body coordinates for each image frame and the external device signal 78 from the differentiable physics engine 77, the kinetic core SDK 76 determines and outputs one or more biomechanical performance parameters 92.

Now, the user input/calibration 70, the kinetic core SDK 76, and the application output 80, 88, 90, 92 of the illustrative biomechanical analysis systems 110, 120, 130, 140, 150 will be described in further detail. In the illustrative embodiments described above, some user input 70 from the system may augment the automatic system calibration tasks performed. One source of input may involve the user selecting the XY pixel location of the four force plate corners from multiple RBG video images. The locations can be triangulated from this information. Additional calibration may require the user to hold an object, such as a checkboard or Aruco pattern. The person holding the calibration target will then perform a sequence of tasks, moving the calibration target at the optimal angle to the respective cameras and to the optimal positions for calibration within the capture volume. Another form of calibration may involve having the user standing on the force plate in the capture volume. The system will capture the user rotating their body around the vertical axis with their arms at 45 degree and 90 degrees of shoulder abduction. The 3D pose estimation system 74 then calibrates based on the plausible parameters (lengths) of the subject's body segment's and combined shape.

Figure 15:
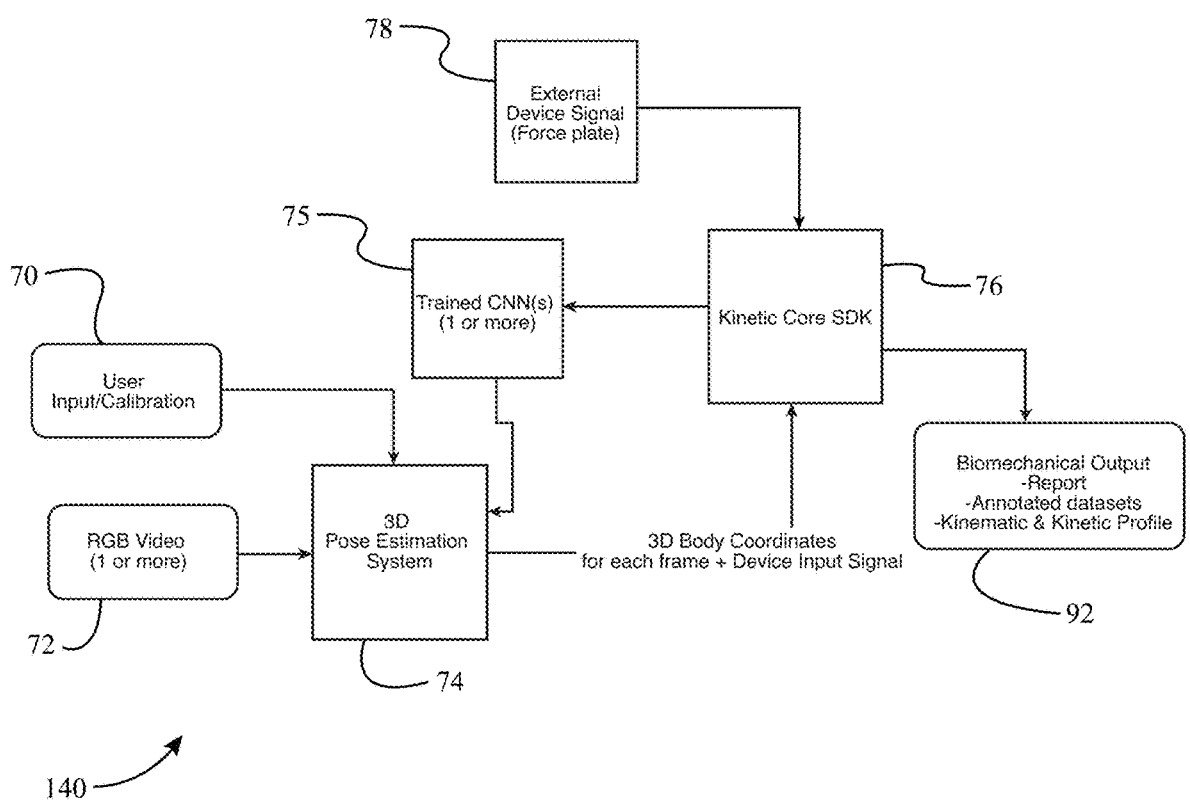
FIG. 15 is a schematic diagram of a fourth illustrative embodiment of biomechanical analysis system.

In the illustrative embodiment of FIG. 15, there are one or more trained CNN modules 75 which are used to obtain better accuracy of the 3D pose estimation system 74. One of these models may be a "plausible physics" model. This model determined the plausibility of the estimated pose in the physical domain. In addition, this model may consider the temporal parameters of the physics, including: (i) body inertia, (ii) ground/floor contact in regards to foot position, (iii) body segment lengths, (iv) body segment angular velocities, and (v) joint ranges of motion. In the illustrative embodiment, an additional CNN may be applied for allowable human poses. This is a general model which will prevent unrealistic body representations and 3D reconstructions.

In the illustrative embodiments of FIGS. 12-16, the desired application output 80, 88, 90, 92 is a biomechanical analysis of the action's performed in the capture volume. This includes output, such as an annotated dataset in which calculated values, such as the rate of force development, maximum force, and other descriptors are displayed. A general report of the movement performed may also be generated and the algorithmically determined kinetic and kinematic insights from both traditional manually devised algorithms and insights derived from machine learned algorithms obtained from analysis of large datasets of similar movements.

The specific output is determined by the movement performed. As an example, analyzing a baseball swing is quite different than analyzing the balance of a subject after physical or visual perturbation. Each has its own key performance indicators (KPIs).

For example, when analyzing baseball and golf swings, the body center of mass needs to be determined. Since the swing involves swinging a bat or club around the body's center of mass, the moment about the instantaneous center of mass of the subject is a KPI. Additionally, the angular velocity of the hips, torso, upper arm, and lower arm are calculated to generate a 4 component time series plot, where the y-axis is the instantaneous angular velocity, and the x-axis is time. This is known as the kinematic sequence.

Specific movements in the capture volume may be analyzed temporally, such that event points common to the movements in question will be automatically detected. In the golf swing example, the beginning of the take away, top of the backswing, and contact event points are timestamped. In baseball, the moment when the forward move toward the pitcher begins and ends is timestamped by analyzing the range of the center of mass. Additionally, the point of foot off and "foot down" of the stride leg event point is outputted.

The 3D pose estimation system 74 also may implement ball tracking metrics. This sub-model will be able to track the spin and velocity of an object moving in the capture volume. The ball tracker timestamps the event points of ball release (on throw) and bat or club contact. It outputs the instantaneous angular velocity and direction of the spin of the object. Additionally, a bat or club tracker may be implemented. This sub-model generates a time series plot of the 3D position of the bat or club in the capture volume relative to the subject and any force plates. The tracker outputs the bat or club path during the swing movements as well as the plane specific and 3D reconstructed view of the bat or club's angular position, velocity, and acceleration. Event points for the maximum angular velocity are time-stamped.

Using the key point information from the 3D pose estimation system 74 and the associated algorithms for movement specific analysis, the system becomes an "expert system" which is capable of diagnosing and providing rehabilitation and training interventions to improve the subject's performance during the tasks performed in the capture volume. This requires a large amount of training data, which is a recording of the actions performed in the capture space.

Additionally, expert annotation of the data may be built into the kinetic core SDK 76. In the case of the baseball and golf application, the software allows the coaches to annotate specific event points, rate the "quality" of the movement, and make any other notes on the subject's performance of the task at hand. All of these inputs are aggregated in the database and a machine learning algorithm is applied to train the expert system. Once the annotated data is fed through the machine learning algorithms, the model is able to output the expert analysis of the swing without the need for the expert practitioner. A swing can automatically be rated by the software and any training interventions or swing suggestions are outputted in the report.

In another illustrative biomechanical application, a therapist may review a captured video and force plate data, and write notes on the performance of the subject and any thoughts regarding their condition. Additionally, the expert may provide a review kinematic analysis while using the force plate data as additional information for making the decision. One key aspect of one biomechanical analysis system is determining the sway strategy of the patient. The kinematic information, derived from the 3D pose estimation system 74 is used by the therapist to determine a "sway strategy" of the patient. In the system, the subject is assumed to use an ankle strategy when regaining their balance in response to a known perturbation of the floor. The therapist may use the kinematic information to rate the strategy and determine if the amount of ankle versus hip movement is acceptable for the test. If deemed acceptable, the strategy employed by the subject and the therapist annotation (acceptable sway strategy or not) will be saved and used to train the algorithm. In time, the algorithm will provide instant feedback to the on the acceptability of the trial's sway strategy and provide a recommendation on how to improve the strategy (i.e.; focus on bending at the ankles and keep the torso upright, etc.).

In one or more illustrative embodiments, the performance of the user suggestions on the sway strategy of the subsequent trial may be used to provide more useful recommendations. By grading the performance on the subsequent trial thousands of times, the machine learned algorithm learns what to suggest to the patient to obtain the desired result.

In one or more illustrative embodiments, depending on the particular application, the kinetic core SDK 76 may have a plurality of different biomechanical outputs, such as (i) an angular velocity of a body segment, (ii) an angular acceleration of a body segment, (iii) a joint angular position in each image frame, (iv) a joint angular velocity profile, (v) a joint angular acceleration profile, (vi) an event timing metric, (vii) a center of mass velocity profile, (viii) a center of mass acceleration profile, (ix) a rate of force or torque development, and (x) a force or torque impulse value. In addition, the kinetic core SDK 76 may output a key point overlay (i.e., visual overlay of the body keypoints in 1 or more 2D images) and/or a 3D reconstruction (i.e., a three dimensional reconstruction of the human skeleton and/or a mesh model that estimates the volume of the body). The event timing metrics outputted by the kinetic core SDK 76 may include: (i) the start of movement, (ii) the end of movement, (iii) a movement specific event point, (iv) a point of 0 COM velocity in a jump, (v) begin of "take-away" and "contact" in golf, and (vi) when foot is in contact with ground and not in contact with ground. The center of mass profile outputted by the kinetic core SDK 76 may include: (i) a maximum jump height, (ii) a range of movement over a specific time range, and (iii) velocity and acceleration profiles of the center of mass. A force signal analysis outputted by the kinetic core SDK 76 may include: (i) golf, baseball, balance, and dynamic movement algorithms for interpreting movements, (ii) rates of force development (i.e., derivative of force-time curve), (iii) "matrix" analysis of multiple force plate systems, (iv) impulse values (i.e., integration of the Force-time curve), and (v) timing of key event points. In addition, the kinetic core SDK 76 may further include automatic movement classification and detection, as well as "expert system" algorithms to provide a recommendation to a system user. For example, the system user is given a recommendation for follow up testing or intervention training to be performed due to correlations seen in populations with similar movement characteristics.

In one or more further illustrative embodiments, the biomechanical analysis systems 110, 120, 130, 140, 150 may further include a sensory output device configured to generate sensory feedback for delivery to a system user. The sensory feedback may comprise at least one of a visual indicator, an audible indicator, and a tactile indicator. For example, the sensory output device may comprise one or more of the types of sensory output devices described in U.S. Pat. No. 9,414,784, the entire disclosure of which is incorporated herein by reference.

In one or more further illustrative embodiments, using the principles of inverse dynamics, the biomechanical analysis systems 110, 120, 130, 140, 150 may further map the energy flow of the subject performing a sporting activity in the capture space in which the goal of the athlete is to transfer the optimal or maximal amount of energy to the piece of sporting equipment. The forces and torques occurring at each joint in the body may be determined by the kinematic positions and ground reaction forces (predicted and/or real) and mapped from the body segments and joints in contact with the force plate to the piece of equipment of interest. Additionally, a temporal plausible physics algorithm may be used to correct for the inertia of the body segments from the previous body movements. Also, the biomechanical analysis systems 110, 120, 130, 140, 150 may automatically calculate joint stresses using inverse dynamics. For example, the biomechanical analysis systems 110, 120, 130, 140, 150 may automatically calculate the knee torque in one such application.

8. Pose Estimation Systems Using Depth Information

Now, with reference to the block diagrams in FIGS. 17 and 18, several illustrative pose estimation systems that utilize depth information will be described. Initially, in the block diagram 160 of FIG. 17, it can be seen that the 3D pose estimation system receives sample input images 162, 164 of a scene from a pair of RGB-D video cameras. The sample input images 162, 164 are inputted into both a first 3D branch pose estimation network 166 and a second 2D branch pose estimation network 174. The first 3D branch pose estimation network 166 generates first and second 3D estimates 168, 170 for the respective first and second sample input images 162, 164. The second 2D branch pose estimation network 174 generates first and second 2D estimates 176, 178 for the respective first and second sample input images 162, 164. Then, the first and second 2D estimates 176, 178 and the depth information from the RGB-D video cameras are inputted into the 3D reconstruction module 172 so that the 3D loss training signal may be generated for the first 3D branch pose estimation network 166.

Next, the illustrative pose estimation system that utilizes depth information will be described in further detail with reference to the block diagram 180 of FIG. 18. The pose estimation system depicted in FIG. 18 is similar in many respects to the pose estimation system of FIG. 2, except that depth channel information from RGB-D video cameras is inputted into a 3D reconstruction module 64 together with the first and second 2D poses 52, 58 so as to increase the accuracy of the pose estimation system. As described above for the system of FIG. 2, during training, the system of FIG. 18 is multi-view: a pair of images $(I_i, I_{i+1})$ simultaneously taken by two consecutive RGB-D cameras is fed into the CNN pose estimators 16, 46. In particular, referring to FIG. 18, the images 12, 14 are fed into the CNN pose estimator 16 of the upper branch during the training of the system, while the images 12, 14 also are fed into the CNN pose estimator 46 of the lower branch during the training of the system. The present system is also self-supervised: the 3D pose (V) 34' generated by the lower branch of the diagram in FIG. 18 using triangulation 60 (i.e., epipolar geometry) is used as a training signal for the CNN 16 in the upper branch 10 of the diagram. During inference, the present method is a monocular method: it takes a single image $(I_i)$ 12 as input and estimates the corresponding 3D pose $(\hat{V}_i)$ 22. In FIG. 18, p represents the soft argmax function, T represents triangulation, and L represents smooth L1 loss. Specifically, with reference again to FIG. 18, during training, the CNN pose estimator 16 of the upper branch 3D CNN module 66 outputs volumetric heatmaps 18, 24 $(\hat{H}_i, \hat{H}_{i+1})$ based on the respective input images 12, 14, while the CNN pose estimator 46 of the lower branch 2D CNN module 68 outputs volumetric heatmaps 48, 54 $(H_i, H_{i+1})$ based on the respective input images 12, 14. A respective soft argmax activation function 20, 26 ($\varphi$) is applied to the volumetric heatmaps 18, 24 $(\hat{H}_i, \hat{H}_{i+1})$ in the upper branch, while a respective soft argmax activation function 50, 56 ($\varphi$) is applied to the volumetric heatmaps 48, 54 $(H_i, H_{i+1})$ in the lower branch. After applying the soft argmax activation functions 20, 26 ($\varphi$) to the respective volumetric heatmaps 18, 24 $(H_i, H_{i+1})$ in the upper branch, the respective 3D poses 22, 28 $(\hat{V}_i, \hat{V}_{i+1})$ are obtained. Similarly, after applying the soft argmax activation functions 50, 56 ($\varphi$) to the respective volumetric heatmaps 48, 54 $(H_i, H_{i+1})$ in the lower branch, the respective 2D poses 52, 58 $(U_i, U_{i+1})$ are obtained. Then, to obtain a 3D pose 34' (V) for corresponding synchronized 2D images, triangulation 60 is utilized in the 3D reconstruction module 64. Then, after triangulation 60 in the 3D reconstruction module 64, the triangulated output is combined with the depth information from the RGB-D cameras in depth-based optimization submodule 62 in order to obtain the estimated 3D pose (V) 34'. Finally, to calculate the loss between the 3D poses 22, 28 ($\hat{V}_i$, $\hat{V}_{i+1}$) predicted by the upper (3D) branch, the 3D pose 34' (V) determined from the lower branch is projected onto corresponding camera space, then loss functions 30, 32 are used to train the upper (3D) branch. The loss functions 30, 32 are used to compare 3D poses 22, 28 ($\hat{V}_i$, $\hat{V}_{i+1}$) from the upper branch to the 3D pose 34' (V) from the lower branch. The objective is to get the 3D poses 22, 28 ($\hat{V}_i$, $\hat{V}_{i+1}$) from the upper branch as close as possible to the 3D pose 34' (V) from the lower branch by means of using the minimization or loss functions 30, 32.

In the training pipeline of the present system (see FIG. 18), there are two branches, each starting with the same pose estimation network 16, 46 (a ResNet followed by a deconvolution network (see ref. [36])). During training, only the pose estimation network 16 in the upper branch is trained; the other one 46 is kept frozen. Because the pose estimation network 46 in the 2D lower branch 40 is kept frozen, the 2D lower branch does not take any feedback from the 3D upper branch (i.e., the 2D lower branch is domain independent). During training, because the lower branch is kept frozen, only weights in the upper branch are learned. Weights are not determined for the lower branch. The upper branch is the network that is being trained.

Figure 17:
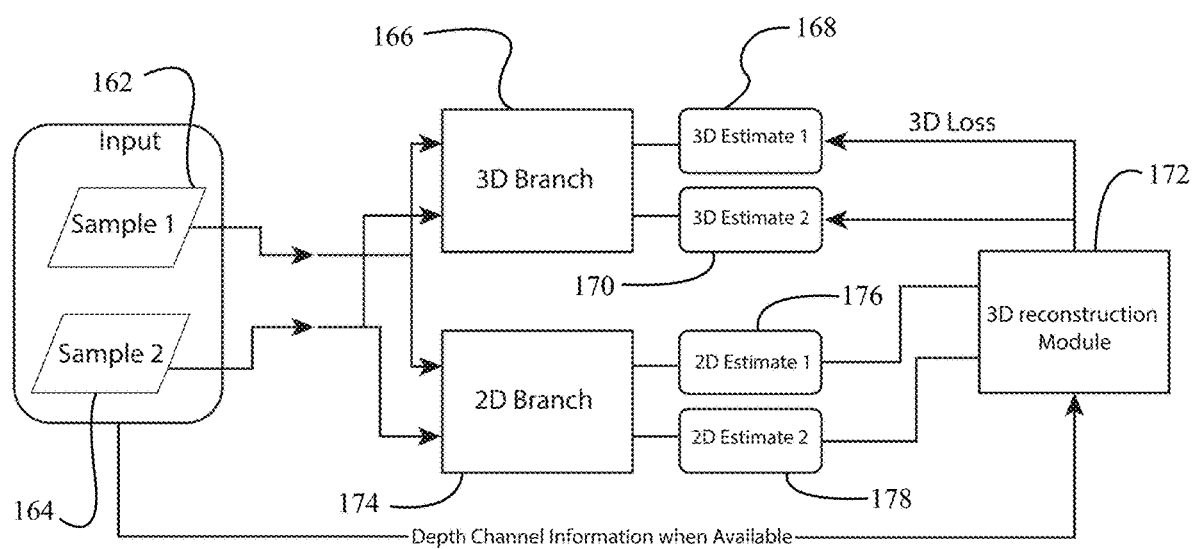
FIG. 17 is a schematic diagram of the overall architecture of a pose estimation system using depth information, according to another illustrative embodiment of the invention.
Figure 18:
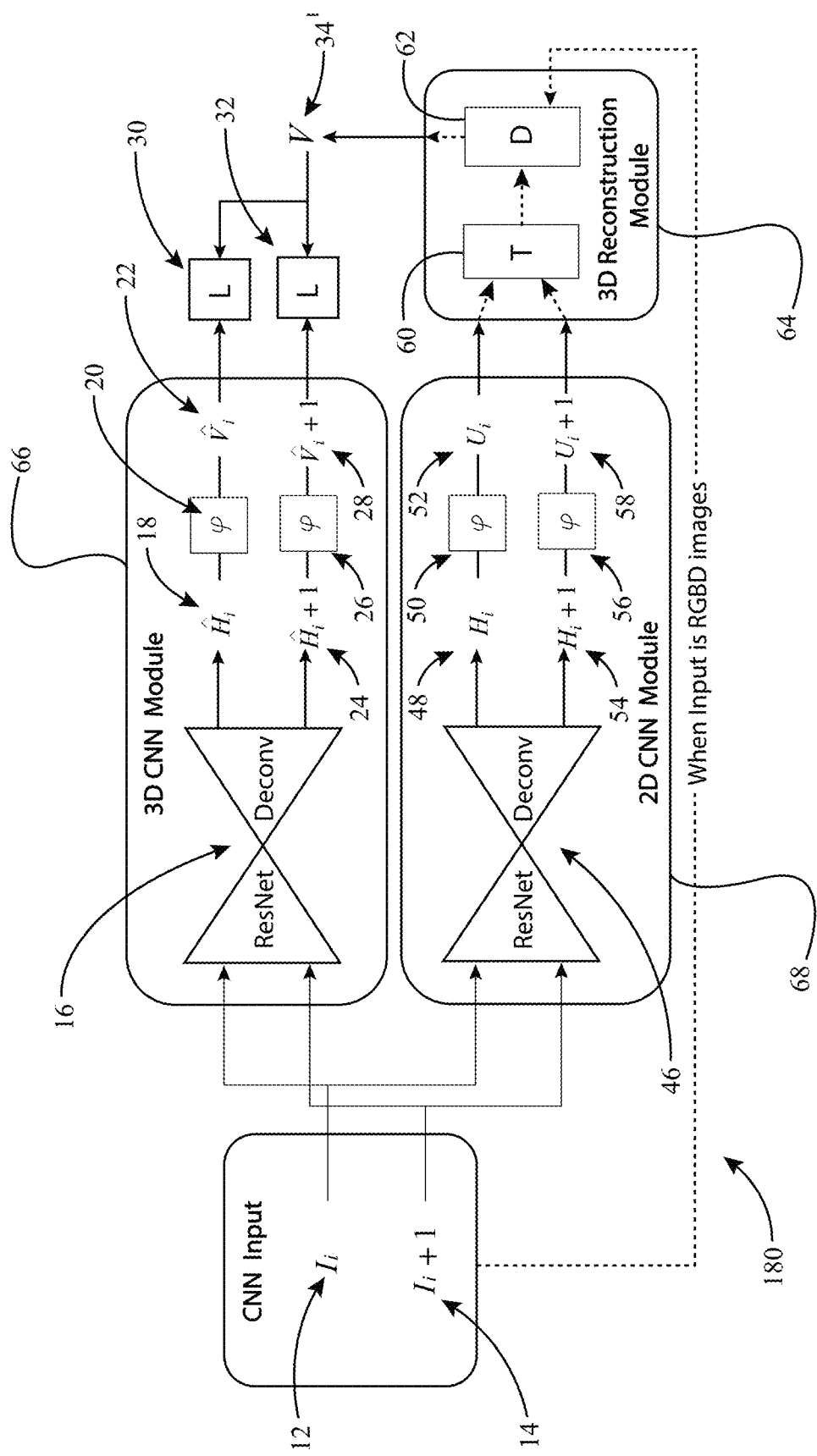
FIG. 18 is another schematic diagram of the overall architecture of the pose estimation system of FIG. 17 that utilizes depth information.

In one or more embodiments of the pose estimation system of FIGS. 17 and 18, the input image samples that are fed into the 3D and 2D branches are RGB-D images instead of RGB images, and the 3D reconstruction module uses depth information to obtain better 3D reconstructions. In these one or more embodiments, an RGB-D image is trained to the 3D body estimation model.

In one or more other embodiments of the pose estimation system of FIGS. 17 and 18, the input image samples are RGB images as in the system of FIG. 2 above, and only the 3D reconstruction module uses depth information (D channel of the RGB-D image) to obtain better 3D reconstructions. In these one or more embodiments, an RGB image is trained to the 3D body estimation model.

In yet one or more other embodiments of the pose estimation system of FIGS. 17 and 18, there is a single input image sample, and the 3D reconstruction module lifts a 2D estimate to 3D depth information. Advantageously, in this manner, models for both RGB and RGB-D inputs can be trained when only a single camera is used.

In still one or more embodiments of the pose estimation system of FIGS. 17 and 18, there are different options for the modules based on the usage of RGB-D images for training. For the CNN input, the options include: (a) two RGB images collected from multiple cameras at the same time instance (as described above for FIG. 2), two RGB-D images collected from multiple cameras at the same time instance, or (c) a single RGB-D image ($I_i$ only). In this option, all the flow from $I_{i+1}$ to $\hat{V}_{i+1}$ and $U_{i+1}$ are discarded. For the 2D and 3D CNN modules 66, 68, the options include: (a) RGB input, or (b) RGB-D input. And, for the 3D reconstruction module 64, the options include: (a) triangulation over 2D keypoint estimations from multiple cameras (as described above for FIG. 2, only submodule T), (b) option (a) followed by a depth-based optimization submodule D, with input as triangulation results and CNN input images $I_i$, $I_{i+1}$ (submodule T followed by submodule D), or (c) a depth-based optimization submodule with input as $U_i$ from 2D CNN module and single CNN input image $I_i$.

In the illustrative embodiment, the pose estimation system of FIGS. 17 and 18 may perform depth-based 3D keypoint optimization. For example, this system may perform the following optimization algorithm steps (depicted by D) to obtain refined 3D keypoints or reconstruct 3D keypoints from 2D keypoints, using depth images where each pixel shows the distance of the corresponding 3D point in space from the camera center: (i) foreground (human) segmentation: foreground is segmented using a thresholding method to produce a mask of the human in the image; (ii) human part segmentation: an off-the-shelf human part segmentation model or SDK of the RGB-D camera is used on RGB channels of input images $I_i$ (and $I_{i+1}$) to generate a human part mask, showing which body part each pixel belongs to; (iii) using the camera parameters and distance from the camera center, each pixel belonging to the human body is back-projected onto 3D world coordinate system; (iv) combining the outputs of step (ii) and (iii) for every camera, a dense point cloud for each human body part is constructed; (v) if there is a single training image $I_i$, 2D keypoint estimate $U_i$ from the 2D branch is backprojected to 3D world coordinate system in the same manner as step (iii) to obtain initial 3D keypoints to be optimized, or if there are two input images $I_i$, $I_{i+1}$, triangulation result is used as initial 3D keypoints to be optimized; and (vi) initial 3D keypoint locations defined in step (v) are jointly optimized using the following geometric and anthropomorphic constraints using a suitable non-convex optimization method. That is, for each body part, the corresponding line segment may be defined using the end keypoints of that part in initial 3D keypoints based upon the following geometric and anthropomorphic constraints: (a) keypoints should lay behind the surface defined by the whole point cloud from each camera viewpoint; (b) line segments connecting neighboring keypoints should have the same direction with the line closest in average to the corresponding part point cloud if it is visible enough; (c) for each body part with enough visibility and its corresponding line segment, variance of the point distances to the line segment should be close to zero; (d) for each body part with enough visibility and its corresponding line segment, average of the point distances to the line segment should be in line with the anthropomorphic data provided in scientific studies (particularly, this average should lay close to the measured average girth data, and the ratio of averages between body parts should align with the body proportion statistics from scientific studies); and (e) for each body part (other than torso) with enough visibility and its corresponding line segment, variance of the point distances to the line segment should be close to zero.

In the illustrative embodiment, based on the aforedescribed options, the pose estimation system can utilize a mix of following training regimes: (1) EpipolarPose training regime of FIG. 2 above: CNN Input Option (a), 2D and 3D CNN Modules Option (a), 3D Reconstruction Module Option (a); (2) Training an RGB to 3D Keypoint Estimator with multiple camera RGBD data: CNN Input Option (b), 2D and 3D CNN Modules Option (a), 3D Reconstruction Module Option (b), in this case, RGB channels of input images are fed into the 2D and 3D CNN Modules and entirety of input images are fed into depth-based optimization submodule D; (3) Training an RGB to 3D Keypoint Estimator with single camera RGBD data: CNN Input Option (c), 2D and 3D CNN Modules Option (a), 3D Reconstruction Module Option (c), in this case, RGB channels of the single input image are fed into the 2D and 3D CNN Modules and entirety of the input image is fed into depth-based optimization submodule D; (4) Training an RGB-D to 3D Keypoint Estimator with multiple camera RGBD data: CNN Input Option (b), 2D and 3D CNN Modules Option (b), 3D Reconstruction Module Option (b), in this case, entirety of input images is fed into the 2D and 3D CNN Modules and depth-based optimization submodule D, and (5) Training an RGB-D to 3D Keypoint Estimator with single camera RGBD data: CNN Input Option (c), 2D and 3D CNN Modules Option (b), 3D Reconstruction Module Option (c), in this case, entirety of a single input image is fed into the 2D and 3D CNN Modules and depth-based optimization submodule D. Training regimes 1, 2, and 3 can be used together with a training set covering all the CNN Input Options to train an RGB to 3D Keypoint Estimation model. Training regimes 4 and 5 can be used together with a training set covering CNN Input Options (b) and (c) to train an RGB-D to 3D Keypoint Estimation model.

9. Additional Pose Estimation Systems Using A 3D Reconstruction Module

Figure 19:
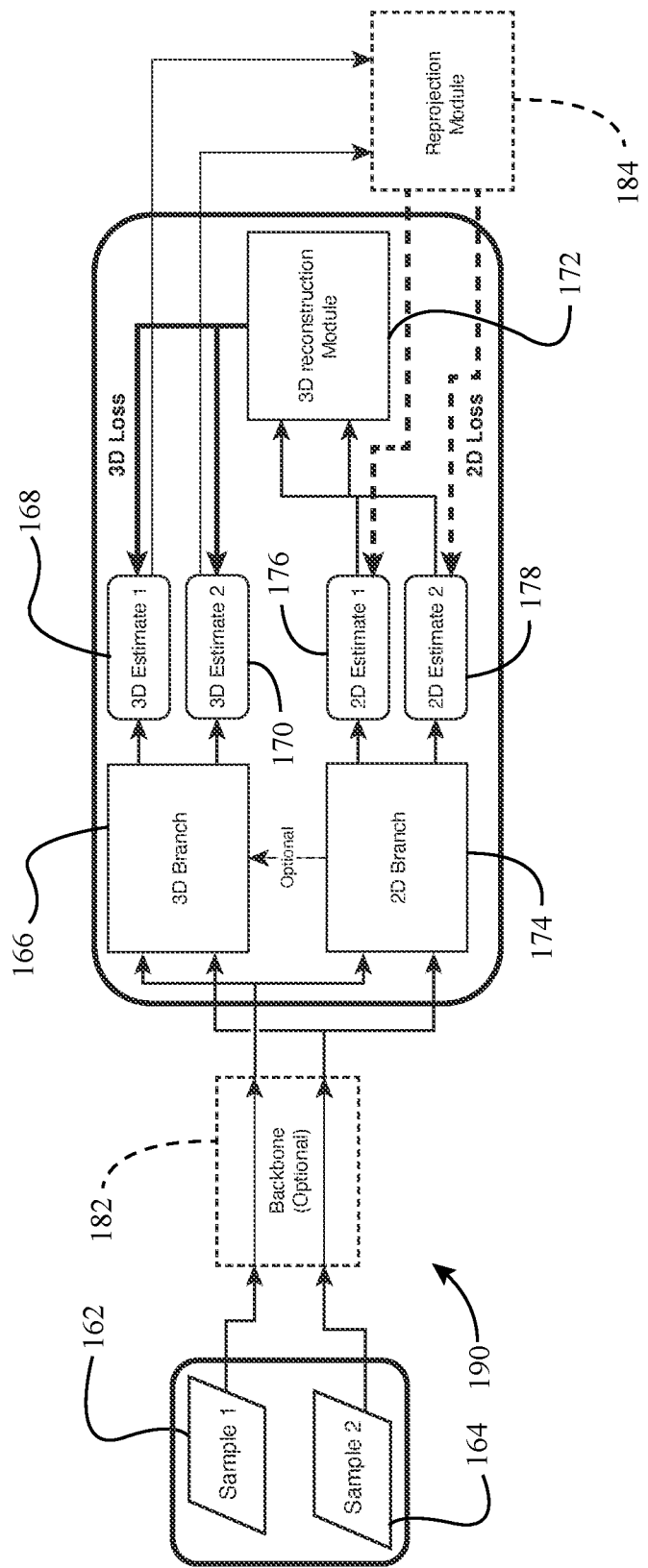
FIG. 19 is a schematic diagram of the overall architecture of a pose estimation system, according to yet another illustrative embodiment of the invention.

Now, with reference to the block diagram in FIG. 19, several additional illustrative pose estimation systems that utilize a 3D reconstruction module will be described. Initially, in the block diagram 190 of FIG. 19, it can be seen that the 3D pose estimation system receives sample input images 162, 164 of a scene from a pair of video cameras. The sample input images 162, 164 are inputted into both a first 3D branch pose estimation neural network 166 and a second 2D branch pose estimation neural network 174. The first 3D branch pose estimation neural network 166 generates first and second 3D estimates 168, 170 for the respective first and second sample input images 162, 164. The second 2D branch pose estimation neural network 174 generates first and second 2D estimates 176, 178 for the respective first and second sample input images 162, 164. Then, the first and second 2D estimates 176, 178 are inputted into the 3D reconstruction module 172 so that the 3D loss training signal may be generated for the first 3D branch pose estimation neural network 166. In addition, as shown in the diagram of FIG. 19, the first and second 3D estimates 168, 170 are inputted into the reprojection module 184 so that the 2D loss training signal may be generated for the second 2D branch pose estimation neural network 174.

The system of FIG. 19 utilizes a training regime where the 3D branch and the 2D branch are both trained in an alternating fashion as described hereinafter. First, the shared backbone 182 processes the sample input images 162, 164 and generates features 1 and 2 that are used for both the 3D and 2D branches 166, 174. Then, features 1 and 2 are processed by both branches 166, 174 and 3D and 2D estimates 168, 170, 176, 178 are generated. The 3D reconstruction module 172 combines 2D estimates 176, 178 by triangulation, and produces a 3D reconstruction of keypoints. The reconstruction produced by the 3D reconstruction module 172 is used to train the upper 3D branch 166. This portion of the training regime is similar to that described above for FIG. 2, except for the shared backbone 182. After the upper 3D branch 166 is trained, the 3D branch 166 is frozen. Then, 3D estimates 168, 170 from the upper 3D branch 166 are processed by reprojection module 184 by performing the following steps: (i) the reprojection module 184 first rigidly aligns 3D estimates, (ii) a refined single 3D estimate is calculated as a weighted average of 3D estimates 168, 170, (iii) the refined 3D estimate is projected to both camera planes, and (iv) projections 1 and 2 are compared to 2D estimates 176, 178, respectively, to generate a training signal for the 2D branch 174. Once these steps performed by the reprojection module 184 are complete, the 3D branch 166 is unfrozen and 2D branch 174 is frozen, and procedure continues with the functionality performed by the 3D reconstruction module 172 described above.

In another illustrative embodiment of a pose estimation system, the system architecture is generally the same as that described above with reference to FIG. 19. However, the types of estimates are different and the 3D reconstruction module 172 and the reprojection module 184 operate accordingly as will be described hereinafter. The 3D branch 166 outputs the vertices of a canonical human mesh model. The 2D branch 174 outputs an index UV map of image pixels where indexed UV values correspond to surface locations on the canonical human mesh. The 3D reconstruction module 172 still performs triangulation, as described above, but with the following additional steps: (i) the UV values in 2D estimates 176, 178 are compared and a set of matching pairs corresponding to the same vertex of the canonical mesh are generated; (ii) for every pair in this set, a 3D point in world coordinates is calculated by triangulation; and (iii) the calculated point set is compared with 3D vertex estimates 168, 170 of the upper 3D branch 166 to generate a training signal for the upper 3D branch 166. The reprojection module 184 generally operates in the same manner as that described above for the preceding illustrative embodiment.

10. Conclusion

It is readily apparent that the aforedescribed three dimensional pose estimation system offer numerous advantages and benefits. First of all, the three dimensional pose estimation system is able to predict three dimensional (3D) human pose from a single image. Secondly, the three dimensional pose estimation system does not require any 3D supervision or camera extrinsics. Finally, the three dimensional pose estimation system is able to create its own 3D supervision by utilizing epipolar geometry and 2D ground-truth poses.

Advantageously, the three dimensional pose estimation system described herein sets the new state-of-the-art among weakly/self-supervised methods for 3D human pose estimation. Also, advantageously, the three dimensional pose estimation system described herein includes a Pose Structure Score (PSS), a new performance measure for 3D human pose estimation to better capture structural errors.

More specifically, it was shown herein that, even without any 3D ground truth data and the knowledge of camera extrinsics, multi-view images can be leveraged to obtain self-supervision. At the core of the present approach, there is a method which can utilize 2D poses from multi-view images using epipolar geometry to self-supervise a 3D pose estimator. The present method achieved state-of-the-art results in Human3.6M and MPI-INF-3D-HP benchmarks among weakly/self-supervised methods. In addition, the weaknesses of localization based metrics, i.e., MPJPE and PCK, for human pose estimation task were discussed, and therefore, a new performance measure, i.e., Pose Structure Score (PSS), was introduced to score the structural plausibility of a pose with respect to its ground truth.

While reference is made throughout this disclosure to, for example, "an illustrative embodiment", "one embodiment", or a "further embodiment", it is to be understood that some or all aspects of these various embodiments may be combined with one another as part of an overall embodiment of the invention. That is, any of the features or attributes of the aforedescribed embodiments may be used in combination with any of the other features and attributes of the aforedescribed embodiments as desired.

Each reference listed below is expressly incorporated by reference herein in its entirety:

[1] S. Amin, M. Andriluka, M. Rohrbach, and B. Schiele. Multiview pictorial structures for 3d human pose estimation. In British Machine Vision Conference, 2013.

[2] M. Andriluka, L. Pishchulin, P. Gehler, and B. Schiele. 2D human pose estimation: New benchmark and state of the art analysis. In IEEE Conference on Computer Vision and Pattern Recognition, 2014.

[3] V. Belagiannis, S. Amin, M. Andriluka, B. Schiele, N. Navab, and S. Ilic. 3D pictorial structures for multiple human pose estimation. In IEEE Conference on Computer Vision and Pattern Recognition, 2014.

[4] V. Belagiannis, S. Amin, M. Andriluka, B. Schiele, N. Navab, and S. Ilic. 3D pictorial structures revisited: Multiple human pose estimation. IEEE Transaction on Pattern Analysis and Machine Intelligence, 2016.

[5] M. Bergtholdt, J. Kappes, S. Schmidt, and C. Schnorr. A study of parts-based object class detection using complete graphs. In International Journal of Computer Vision, 2010.

[6] M. Burenius, J. Sullivan, and S. Carlsson. 3D pictorial structures for multiple view articulated pose estimation. In IEEE Conference on Computer Vision and Pattern Recognition, 2013.

[7] Z. Cao, T. Simon, S.-E. Wei, and Y. Sheikh. Realtime multiperson 2d pose estimation using part affinity fields. In IEEE Conference on Computer Vision and Pattern Recognition, 2017.

[8] C.-H. Chen and D. Ramanan. 3D human pose estimation=2D pose estimation+matching. In IEEE Conference on Computer Vision and Pattern Recognition, 2017.

[9] D. Drover, R. MV, C.-H. Chen, A. Agrawal, A. Tyagi, and C. P. Huynh. Can 3d pose be learned from 2d projections alone? European Conference on Computer Vision Workshops, 2018.

[10] A. Elhayek, E. de Aguiar, A. Jain, J. Thompson, L. Pishchulin, M. Andriluka, C. Bregler, B. Schiele, and C. Theobalt. MARCOnI-ConvNet-based MARker-less motion capture in outdoor and indoor scenes. IEEE Transaction on Pattern Analysis and Machine Intelligence, 2017.

[11] A. Elhayek, E. de Aguiar, A. Jain, J. Tompson, L. Pishchulin, M. Andriluka, C. Bregler, B. Schiele, and C. Theobalt. Efficient ConvNet-based marker-less motion capture in general scenes with a low number of cameras. In IEEE Conference on Computer Vision and Pattern Recognition, 2015.

[12] H.-S. Fang, Y. Xu, W. Wang, X. Liu, and S.-C. Zhu. Learning pose grammar to encode human body configuration for 3D pose estimation. In Association for the Advancement of Artificial Intelligence, 2018.

[13] R. I. Hartley and P. Sturm. Triangulation. Computer Vision and Image Understanding, 1997.

[14] K. He, X. Zhang, S. Ren, and J. Sun. Deep residual learning for image recognition. In IEEE Conference on Computer Vision and Pattern Recognition, 2016.

[15] S. Ioffe and C. Szegedy. Batch normalization: Accelerating deep network training by reducing internal covariate shift. In Journal of Machine Learning Research, 2015.

[16] C. Ionescu, D. Papava, V. Olaru, and C. Sminchisescu. Human3.6m: Large scale datasets and predictive methods for 3D human sensing in natural environments. In IEEE Transaction on Pattern Analysis and Machine Intelligence, 2014.

[17] D. P. Kingma and J. Ba. Adam: A method for stochastic optimization. In International Conference on Learning Representations, 2015.

[18] M. Kocabas, S. Karagoz, and E. Akbas. Multiposenet: Fast multi-person pose estimation using pose residual network. In European Conference on Computer Vision, 2018.

[19] S. Li and A. B. Chan. 3D human pose estimation from monocular images with deep convolutional neural network. In Asian Conference on Computer Vision, 2014.

[20] T.-Y. Lin, M. Maire, S. Belongie, J. Hays, P. Perona, D. Ramanan, P. Dollar, and C. L. Zitnick. Microsoft COCO: Common objects in context. In European Conference on Computer Vision, 2014.

[21] A. L. Maas, A. Y. Hannun, and A. Y. Ng. Rectifier nonlinearities improve neural network acoustic models. In International Conference on Machine Learning, 2013.

[22] J. Martinez, R. Hossain, J. Romero, and J. J. Little. A simple yet effective baseline for 3D human pose estimation. In International Conference on Computer Vision, 2017.

[23] D. Mehta, H. Rhodin, D. Casas, P. Fua, O. Sotnychenko, W. Xu, and C. Theobalt. Monocular 3D human pose estimation in the wild using improved cnn supervision. In International Conference on 3DVision, 2017.

[24] F. Moreno-Noguer. 3D human pose estimation from a single image via distance matrix regression. In IEEE Conference on Computer Vision and Pattern Recognition, 2017.

[25] A. Newell, K. Yang, and J. Deng. Stacked hourglass networks for human pose estimation. In European Conference on Computer Vision, 2016.

[26] D. Nister. An efficient solution to the five-point relative pose problem. IEEE Transaction on Pattern Analysis and Machine Intelligence, 2004.

[27] A. Paszke, S. Gross, S. Chintala, G. Chanan, E. Yang, Z. De-Vito, Z. Lin, A. Desmaison, L. Antiga, and A. Lerer. Automatic differentiation in pytorch. In International Conference on Learning Representations, 2017.

[28] G. Pavlakos, X. Zhou, and K. Daniilidis. Ordinal depth supervision for 3D human pose estimation. In IEEE Conference on Computer Vision and Pattern Recognition, 2018.

[29] G. Pavlakos, X. Zhou, K. G. Derpanis, and K. Daniilidis. Coarse-to-fine volumetric prediction for single-image 3D human pose. In IEEE Conference on Computer Vision and Pattern Recognition, 2017.

[30] G. Pavlakos, X. Zhou, K. G. Derpanis, and K. Daniilidis. Harvesting multiple views for marker-less 3d human pose annotations. In IEEE Conference on Computer Vision and Pattern Recognition, 2017.

[31] H. Rhodin, J. Sporri, I. Katircioglu, V. Constantin, F. Meyer, E. Muller, M. Salzmann, and P. Fua. Learning monocular 3d human pose estimation from multi-view images. In IEEE Conference on Computer Vision and Pattern Recognition, 2018.

[32] G. Rogez, P. Weinzaepfel, and C. Schmid. Lcr-net: Localization-classification-regression for human pose. In IEEE Conference on Computer Vision and Pattern Recognition, 2017.

[33] M. Sanzari, V. Ntouskos, and F. Pirri. Bayesian image based 3d pose estimation. In European Conference on Computer Vision, 2016.

[34] I. Sarandi, T. Linder, K. O. Arras, and B. Leibe. How robust is 3d human pose estimation to occlusion? In IROS Workshop—Robotic Co-workers 4.0, 2018.

[35] X. Sun, J. Shang, S. Liang, and Y. Wei. Compositional human pose regression. In International Conference on Computer Vision, 2017.
[36] X. Sun, B. Xiao, F. Wei, S. Liang, and Y. Wei. Integral human pose regression. In European Conference on Computer Vision, 2018.
[37] S. Suwajanakorn, N. Snavely, J. Tompson, and M. Norouzi. Discovery of latent 3d keypoints via end-to-end geometric reasoning. In Advances in Neural Information Processing, 2018.
[38] P. K. J. T. Tejas D Kulkarni, William F Whitney. Deep convolutional inverse graphics network. In Advances in Neural Information Processing, 2015.
[39] B. Tekin, I. Katircioglu, M. Salzmann, V. Lepetit, and P. Fua. Structured prediction of 3D human pose with deep neural networks. In British Machine Vision Conference, 2016.
[40] B. Tekin, P. Marquez-Neila, M. Salzmann, and P. Fua. Learning to fuse 2D and 3D image cues for monocular body pose estimation. In International Conference on Computer Vision, 2017.
[41] D. Tome, C. Russell, and L. Agapito. Lifting from the deep: Convolutional 3D pose estimation from a single image. In IEEE Conference on Computer Vision and Pattern Recognition, 2017.
[42] H.-Y. F. Tung, A. W. Harley, W. Seto, and K. Fragkiadaki. Adversarial inverse graphics networks: Learning 2d-to-3d lifting and image-to-image translation from unpaired supervision. In International Conference on Computer Vision, 2017.
[43] L. van der Maaten and G. Hinton. Visualizing data using t-sne. In Journal of Machine Learning Research.
[44] S.-E. Wei, V. Ramakrishna, T. Kanade, and Y. Sheikh. Convolutional pose machines. In IEEE Conference on Computer Vision and Pattern Recognition, 2016.
[45] J. Wu, T. Xue, J. J. Lim, Y. Tian, J. B. Tenenbaum, A. Torralba, and W. T. Freeman. Single image 3d interpreter network. In European Conference on Computer Vision (ECCV), 2016.
[46] B. Xiaohan Nie, P. Wei, and S.-C. Zhu. Monocular 3d human pose estimation by predicting depth on joints. In International Conference on Computer Vision, 2017.
[47] X. Zhou, M. Zhu, K. Derpanis, and K. Daniilidis. Sparseness meets deepness: 3D human pose estimation from monocular video. In IEEE Conference on Computer Vision and Pattern Recognition, 2016.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A system for estimating a three dimensional pose of one or more persons in a scene, the system comprising:
one or more cameras, the one or more cameras configured to capture one or more images of the scene; and
a data processor including at least one hardware component, the data processor configured to execute computer executable instructions, the computer executable instructions comprising instructions for:
receiving the one or more images of the scene from the one or more cameras;
extracting features from the one or more images of the scene for providing inputs to a first branch pose estimation neural network;
extracting features from the one or more images of the scene for providing inputs to a second branch pose estimation neural network;
generating a first training signal from the second branch pose estimation neural network using a three dimensional reconstruction module for input into the first branch pose estimation neural network, the three dimensional reconstruction module generating an estimated three dimensional pose by performing triangulation on one or more two dimensional estimated poses generated by the second branch pose estimation neural network;
generating one or more volumetric heatmaps using the first branch pose estimation neural network; and
applying a maximization function to the one or more volumetric heatmaps to obtain a three dimensional pose of one or more persons in the scene.

2. The system according to claim 1, wherein, during the training of the system, the data processor is further configured to execute computer executable instructions for:
calculating the loss between one or more three dimensional poses generated by the first branch pose estimation neural network and the estimated three dimensional pose generated by the three dimensional reconstruction module using a loss function; and
generating the first training signal for the first branch pose estimation neural network based upon the calculated loss.

3. The system according to claim 2, wherein the loss function utilized by the data processor comprises a smooth L1 loss function.

4. The system according to claim 1, wherein the data processor is configured to extract the features from the one or more images of the scene using one or more residual networks followed by one or more deconvolution networks, which together form a shared backbone feature extractor for the first branch pose estimation neural network and the second branch pose estimation neural network.

5. The system according to claim 1, wherein, during the training of the system, the data processor is further configured to execute computer executable instructions for:
generating a second training signal from the first branch pose estimation neural network using a reprojection module for input into the second branch pose estimation neural network, the reprojection module comparing 3D-to-2D point projections generated based upon output from the first branch pose estimation neural network to the one or more two dimensional estimated poses generated by the second branch pose estimation neural network.

6. The system according to claim 5, wherein, during the training of the system, the data processor is further configured to execute computer executable instructions for:
rigidly aligning, using the reprojection module, a plurality of three dimensional estimated poses generated by the first branch pose estimation neural network;
calculating, using the reprojection module, a refined single three dimensional estimated pose as a weighted average of the plurality of rigidly aligned three dimensional estimated poses; and projecting, using the reprojection module, the refined single three dimensional estimated pose to a plurality of camera planes to create the 3D-to-2D point projections.

7. The system according to claim 1, wherein the first branch pose estimation neural network outputs estimated vertices of a canonical human mesh model.

8. The system according to claim 7, wherein the second branch pose estimation neural network outputs an index UV map of image pixels where indexed UV values correspond to surface locations on the canonical human mesh model.

9. The system according to claim 8, wherein, during the training of the system, the data processor is further configured to execute computer executable instructions for:
comparing, using the three dimensional reconstruction module, the indexed UV values generated by the second branch pose estimation neural network, and generating a set of matching pairs of the indexed UV values that correspond to the same estimated vertex of the canonical human mesh model;
for each pair in the set, calculating using the three dimensional reconstruction module, a 3D point in world coordinates using triangulation so as to form a calculated point set; and
comparing the calculated point set with the estimated vertices generated from the first branch pose estimation neural network to generate the first training signal for the first branch pose estimation neural network.

10. The system according to claim 1, wherein the maximization function applied to the one or more volumetric heatmaps by the data processor comprises a soft argmax function.

11. The system according to claim 1, wherein, during the training of the system, the data processor is further configured to train the first branch pose estimation neural network while the second branch pose estimation neural network is kept frozen.

12. The system according to claim 1, wherein, during the training of the system, the data processor is further configured to train the second branch pose estimation neural network while the first branch pose estimation neural network is kept frozen.

* * * * *